(12) United States Patent
Shalev et al.

(10) Patent No.: US 12,251,186 B2
(45) Date of Patent: *Mar. 18, 2025

(54) FULL-SCANNER BARRIER FOR AN INTRA-ORAL DEVICE

(71) Applicant: Align Technology, Inc., San Jose, CA (US)

(72) Inventors: Ariel Shalev, Beit Shemesh (IL); Eran Green, Haifa (IL); Zakhar Ginzburg, Netanya (IL); Matthew Durban, San Jose, CA (US); Roee Gorfinkel, Yavne (IL); Ofer Saphier, Rehovot (IL); Tal Verker, Ofra (IL); Nir Makmel, Tel Aviv (IL); Eran Ishay, Tel Aviv (IL); Raphael Levy, Jerusalem (IL)

(73) Assignee: Align Technology, Inc., San Jose, CA (US)

( * ) Notice: Subject to any disclaimer, the term of this patent is extended or adjusted under 35 U.S.C. 154(b) by 27 days.

This patent is subject to a terminal disclaimer.

(21) Appl. No.: 18/449,660

(22) Filed: Aug. 14, 2023

(65) Prior Publication Data

US 2024/0033029 A1 Feb. 1, 2024

Related U.S. Application Data

(63) Continuation of application No. 16/942,616, filed on Jul. 29, 2020, now Pat. No. 11,759,277.

(Continued)

(51) Int. Cl.
*A61B 6/51* (2024.01)
*A61B 46/00* (2016.01)
*A61B 46/17* (2016.01)

(52) U.S. Cl.
CPC .............. *A61B 46/17* (2016.02); *A61B 6/512* (2024.01); *A61B 46/40* (2016.02)

(58) Field of Classification Search
None
See application file for complete search history.

(56) References Cited

U.S. PATENT DOCUMENTS 5,013,161 A 5/1991 Zaragoza et al.
5,133,606 A * 7/1992 Zaragoza ............... G01K 13/20
374/170

(Continued)

FOREIGN PATENT DOCUMENTS

CN 105120791 A 12/2015
CN 105796047 A 7/2016
CN 108882945 A 11/2018

*Primary Examiner* — David P Porta
*Assistant Examiner* — Mamadou Faye
(74) *Attorney, Agent, or Firm* — Shay Glenn LLP

(57) ABSTRACT

Removable barrier devices for covering an intraoral scanner. The barrier device includes a cover that is adapted to fit over a probe of the scanner. The cover includes a distal portion having walls defining an internal cavity for accommodating a distal end of the probe and formed of a first material, wherein at least one of the walls includes at least one window for allowing transmission of an optical signal between the probe and an external environment. The cover also includes a proximal portion coupled to the distal portion. The barrier device also includes a flexible sleeve adapted to cover a handle of the scanner, the flexible sleeve coupled to the proximal portion of the cover at an interface region configured to prevent fluid from passing through the barrier device between the cover and the sleeve.

23 Claims, 31 Drawing Sheets

Related U.S. Application Data

(60) Provisional application No. 63/004,413, filed on Apr. 2, 2020, provisional application No. 62/955,662, filed on Dec. 31, 2019, provisional application No. 62/955,310, filed on Dec. 30, 2019, provisional application No. 62/880,040, filed on Jul. 29, 2019.

(56) References Cited

U.S. PATENT DOCUMENTS

| | | | |
|---|---|---|---|
| 5,865,621 | A | 2/1999 | Calderwood |
| 5,921,776 | A | 7/1999 | Heilbrunn |
| 6,847,490 | B1 * | 1/2005 | Nordstrom ......... A61B 1/00142 600/407 |
| D925,739 | S | 7/2021 | Shalev et al. |
| 11,134,848 | B2 | 10/2021 | Bala et al. |
| RE49,605 | E | 8/2023 | Kopelman et al. |
| 11,759,277 | B2 * | 9/2023 | Shalev ............... A61B 46/17 600/121 |
| 2004/0156626 | A1 * | 8/2004 | Thoms ............... A61B 1/247 396/17 |
| 2004/0231772 | A1 | 11/2004 | Leonard et al. |
| 2006/0047190 | A1 * | 3/2006 | Jenkins ............... A61B 5/0088 600/340 |
| 2010/0089654 | A1 * | 4/2010 | Williams ............ E21B 33/085 29/402.08 |
| 2015/0100047 | A1 | 4/2015 | Wilt et al. |
| 2015/0378243 | A1 * | 12/2015 | Kippelen ............ G02F 1/3523 359/244 |
| 2017/0303833 | A1 * | 10/2017 | Lonsinger ......... A61B 5/14552 |
| 2021/0121049 | A1 | 4/2021 | Rudnitsky et al. |
| 2021/0128281 | A1 | 5/2021 | Peleg |
| 2021/0137653 | A1 | 5/2021 | Saphier et al. |
| 2021/0196152 | A1 | 7/2021 | Saphier et al. |

* cited by examiner

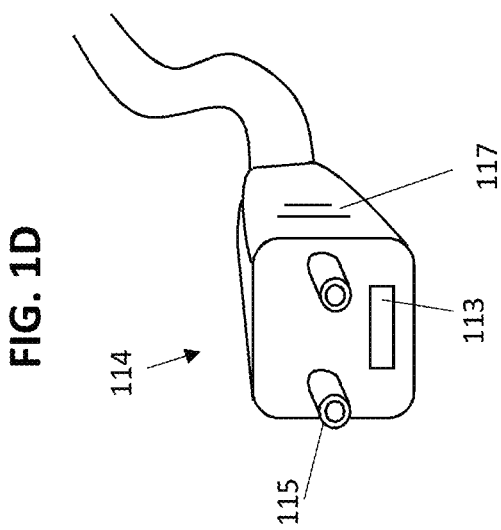
FIG. 1D
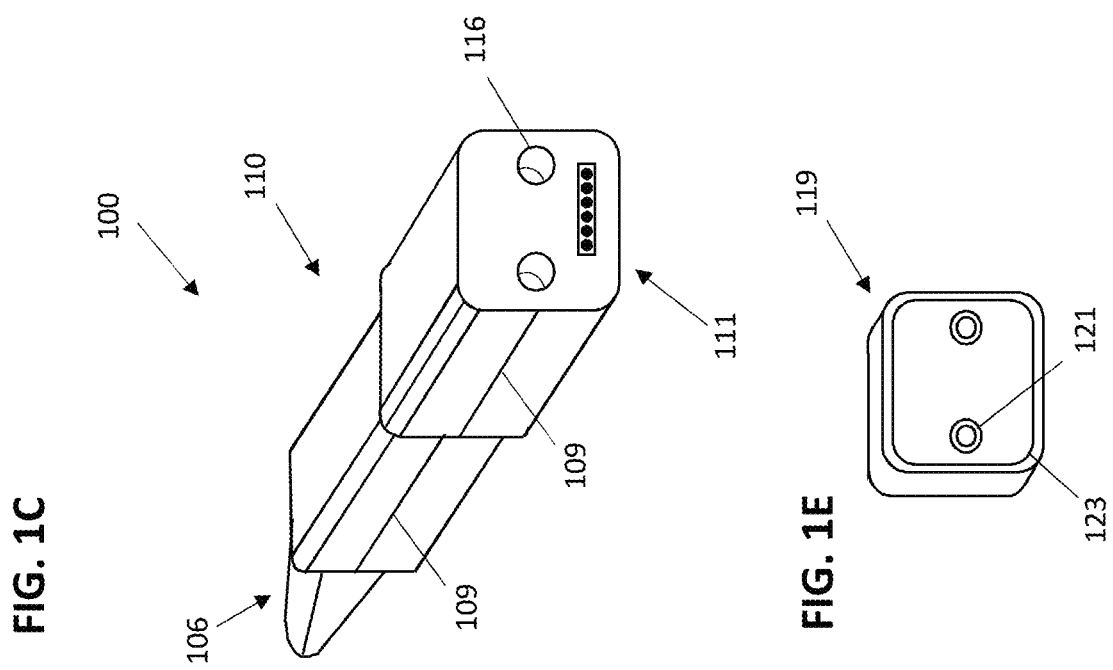
FIG. 1C
FIG. 1E

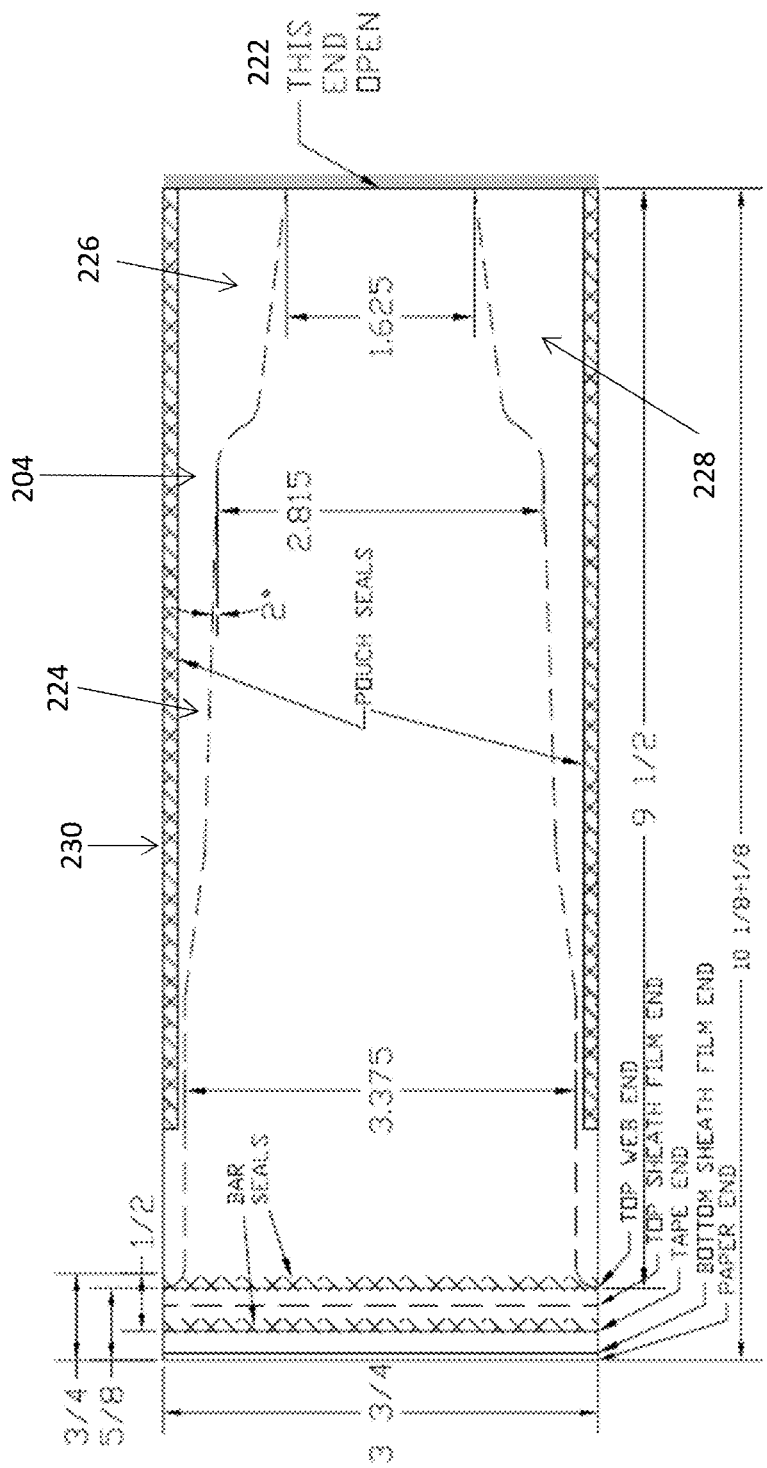
FIG. 2D1

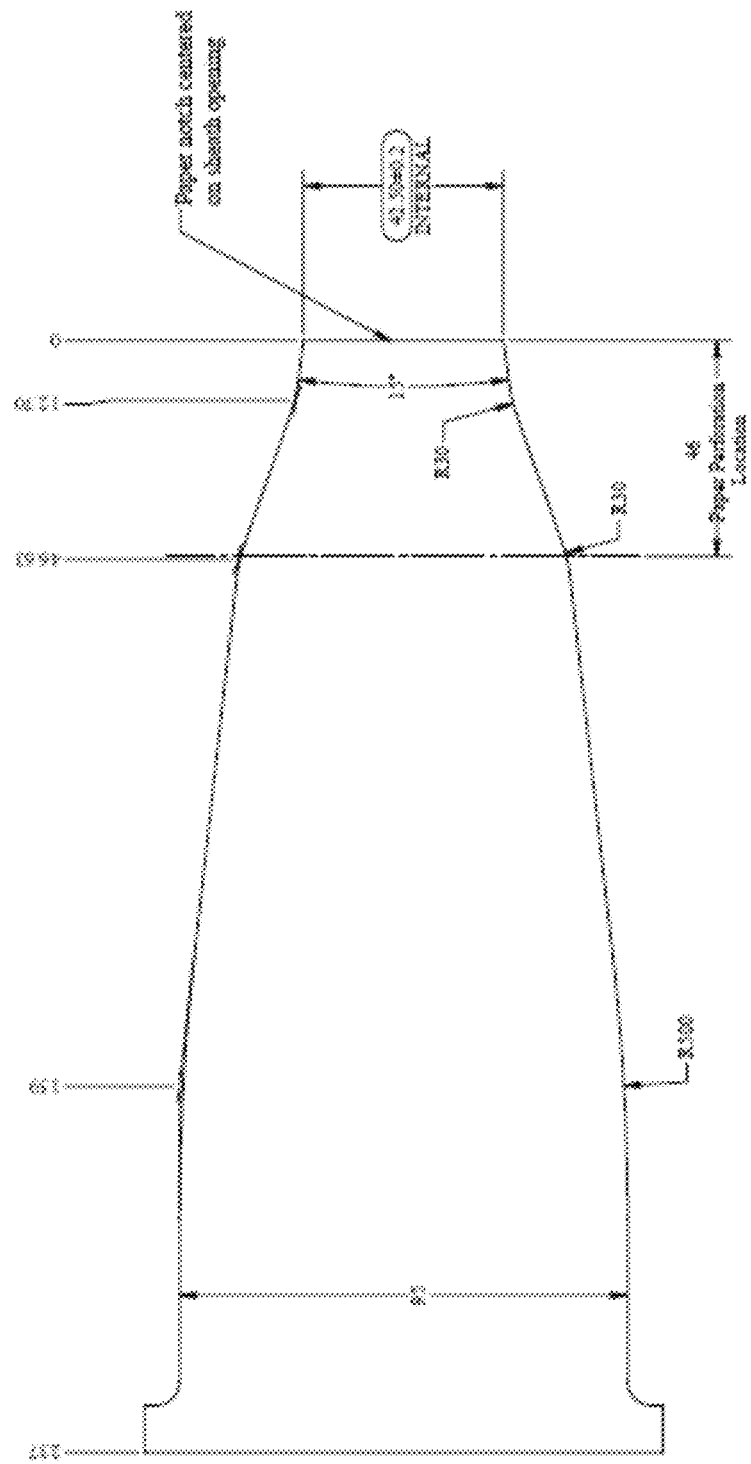
FIG. 2D2

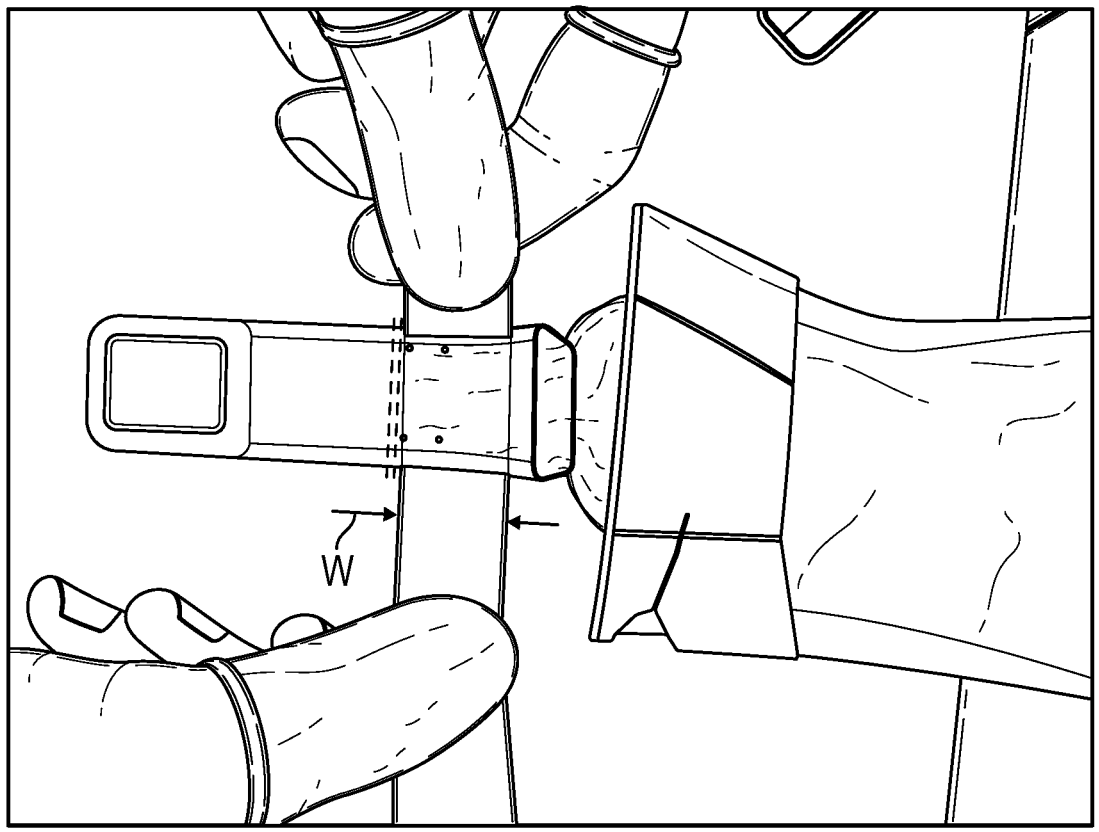
FIG. 2F1

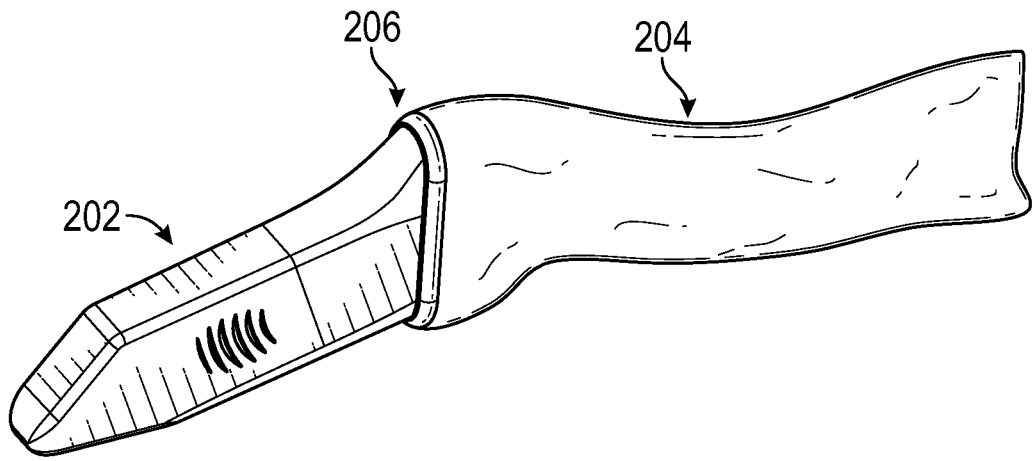
FIG. 2F2
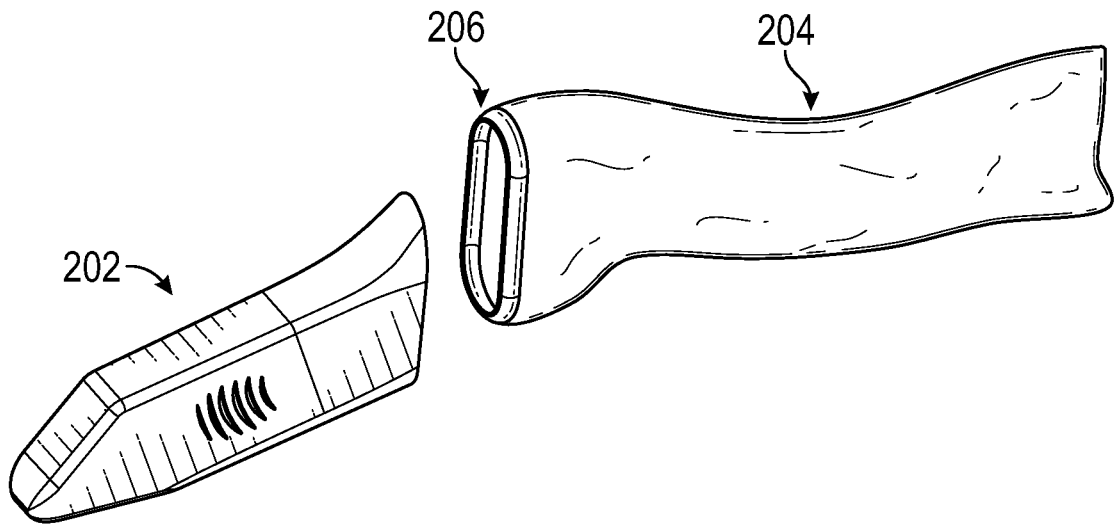
FIG. 2F3
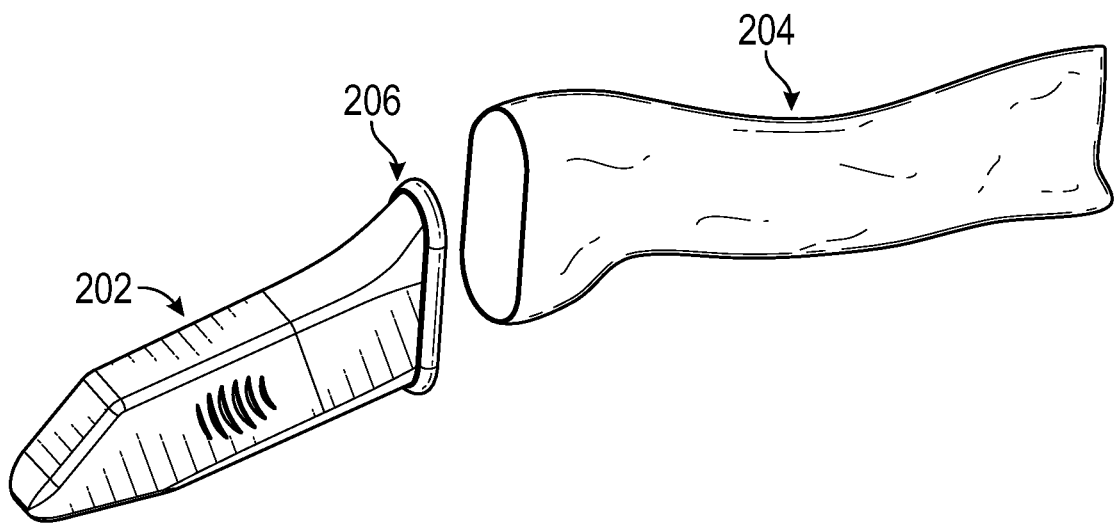
FIG. 2F4

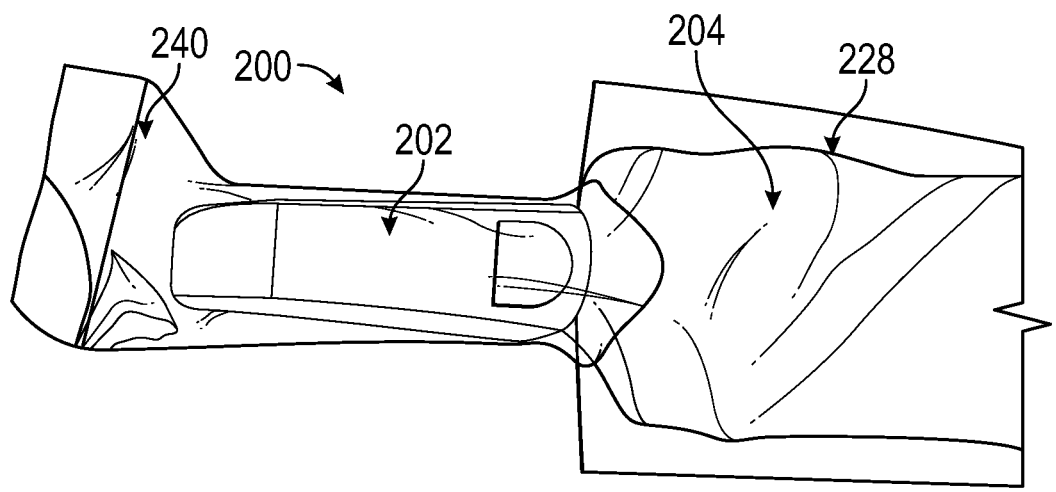
FIG. 2G1
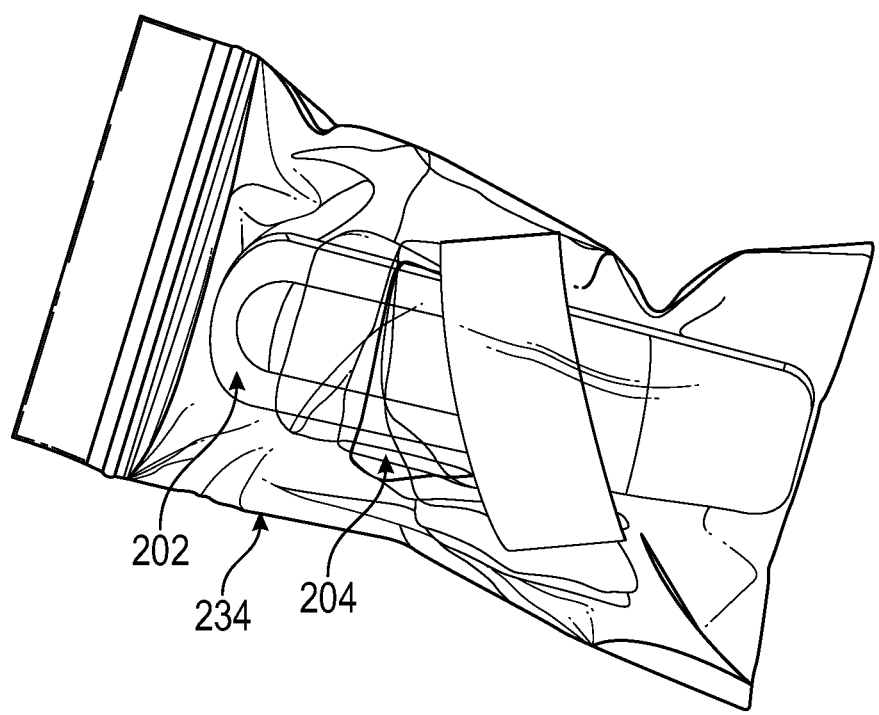
FIG. 2G2

FULL-SCANNER BARRIER FOR AN INTRA-ORAL DEVICE

CROSS REFERENCE TO RELATED APPLICATIONS

This application is a continuation of U.S. patent application Ser. No. 16/942,616, filed on Jul. 29, 2020, titled "FULL-SCANNER BARRIER FOR AN INTRA-ORAL DEVICE," now U.S. Patent Application Publication No. 2021/0030503, which claims priority to U.S. Provisional Patent Application No. 62/880,040, filed on Jul. 29, 2019 and titled "COMPOSITE FULL-SCANNER BARRIER FOR AN INTRA-ORAL DEVICE," U.S. Provisional Patent Application No. 62/955,310, filed on Dec. 30, 2019 and titled "COMPOSITE FULL-SCANNER BARRIER FOR AN INTRA-ORAL DEVICE," U.S. Provisional Patent Application No. 62/955,662, filed on Dec. 31, 2019 and titled "INTRAORAL SCANNER SLEEVE AUTHENTICATION AND IDENTIFICATION," and U.S. Provisional Patent Application No. 63/004,413, filed on Apr. 2, 2020 and titled "COMPOSITE FULL-SCANNER BARRIER FOR AN INTRA-ORAL DEVICE." Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Biological barrier coverings for medical devices having optical components such as intraoral dental scanning devices are described.

BACKGROUND

Surfaces of medical devices can serve as reservoirs for microorganisms that can cause infection in patients and healthcare workers due to cross-contamination. Pathogen transmission can occur directly when a patient or healthcare working comes into direct contact with a contaminated object, or indirectly when a health-care worker's hand or glove becomes contaminated by touching a contaminated object, after which they touch the patient with the contaminated hand or glove. In the case of medical devices, care must be taken to prevent such direct or indirect cross-contamination since these devices are often handled by health-care workers and come near or contact patients.

One way of preventing cross-contamination is to sanitize the entire medical device between uses on patients. However, care must be taken to assure sanitizing procedures adequately disinfect the medical device between use on patients, especially if surfaces of the medical device has crevices and cavities where the contaminates may linger. Another way of reducing cross-contamination is to cover all surfaces of the medical device with a flexible sheet of polymer material, such as a plastic bag or liner, which can be disposed after use on one patient and replaced with a new bag or liner when used on another patient. For example, camera probes and ultrasound scanning devices are often covered with a disposable plastic bag. However, a simple sheet of plastic material may not be appropriate for some types of scanner devices. For example, certain optical scanners can be configured to transmit and/or receive optical signals (e.g., light) at high levels of precision in order to form images with appropriate resolution. In such cases, a flexible plastic material placed over such optical scanner may interfere with proper imaging. For example, the plastic may not be sufficiently transmissive and/or the material may move (e.g., shift and slide) during a scanning operation thereby interfering with reliable transmission of the optical signal to and/or from the device.

What is needed, therefore, is improved biological barrier coverings for medical devices.

SUMMARY

A barrier device for an intraoral scanner may prevent contamination of the intraoral scanner without interfering with the operation of the scanner. The barrier devices described herein can be used to cover medical devices to provide a biological barrier between the medical device and an external environment. The barrier devices can reduce the chances of direct and indirect cross-contamination, and in some cases protect the medical device from damage. As described herein, a barrier device, or portions of the barrier device, may be referred to as a cover, a covering, a protector, a sleeve, a sheath, or simply a barrier.

According to some embodiments, the barrier devices are configured to cover optical scanning devices (also referred to herein as a scanner, scanning device, scanning system, or optical device), such as intraoral dental scanning devices for imaging a patient's dentition. The barrier device can include one or more windows that is adapted to allow transmission of optical signals to and/or from the scanning device. The window may be made a material that is at least partially optically transparent. In some cases, the window includes optically transparent glass, quartz, sapphire and/or an optically transparent polymer material. In some cases, the window is integrally formed in the barrier. The barrier device can be configured to align the window of the barrier device with an optical component, such as an optical device window, of the scanning device. The barrier device can be configured to maintain the window in a fixed position with respect to an optical component, for example, during a scanning operation. In some variations the barrier device is integral with the window (e.g., formed as a single, unitary, piece, and in some variations of the same material). The window may be connected to the barrier device and may be sealed to the barrier device, e.g., by welding, adhesion, or the like.

The barrier device may include different portions have features adapted to cover different corresponding portions of the scanning device. For example, the barrier device can include a cover for covering a scanning portion of the scanner and a sleeve for covering a handle of the scanner. The cover and the sleeve can be made of one or more materials that are substantially impervious to contaminants; the cover and sleeve may be made of the same material and may be integral with each other (e.g., formed as a single, unitary, continuous component) or may be made of different materials. The cover may be relatively rigid, or include rigid sections, for maintaining the window in alignment with respect to an optical component of the scanner. The sleeve may be relatively flexible to allow a user to manipulate buttons, switches or touchpads on the handle of the scanner.

A barrier device may include an interface region that connects the cover and sleeve, which can also be substantially impervious to contaminants and provide a seal to prevent biological material from passing between the cover and the sleeve. In some cases, the interface region provides a hermetic seal between the cover and the sleeve (and/or between the barrier device and the scanner or region of the scanner). According to some embodiments, the interface region includes an adhesive tape, which may have a prescribed width for providing a sufficient seal. In some cases, the interface region includes a clip that releasably couples the cover and the sleeve. In some cases, the interface region includes a welded region, where the material(s) of the cover and the sleeve are welded (e.g., melted) together.

The barrier devices described herein can include a cover made of two or more materials. A first portion of the cover may be made of a first material sufficiently rigid and optically transparent to cover the region of the scanning probe that transmits and receives optical signals. A second portion of the cover may be made of a second material that is moldable and/or weldable to the first portion and the sleeve to form a sealed barrier device effective for acting as a biological barrier for the intraoral scanner probe.

According to some embodiments, the window of barrier device is integrally formed with at least a portion of the cover during a molding operations. For example, the walls and the window may be formed during an injection molding process, whereby the window and the walls are both made of an optically transparent polymer. The thickness of the window and/or walls and injection molding process itself may be specified to provide a sufficiently transparent and uniform window.

According to some embodiments, the window of the barrier device is formed separately from the walls of the cover. In one implementation, the walls of the cover are formed using an injection molding process, and the window is adhesively coupled to the cover. The window may be positioned with respect to an opening of the cover to allow transmission of optical signal through the cover.

The barrier devices described herein are well suited for providing a biological barrier for intraoral optical scanning systems, such as the iTero® scanner and other scanning devices and systems manufactured by ALIGN TECHNOLOGY, INC., having headquarters in San Jose, California, U.S.A. The barrier devices described herein may include any of the features of the optical scanning devices and protective sleeves described in U.S. patent application Ser. No. 16/105,916, filed Aug. 20, 2018, titled "PROTECTIVE SLEEVE FOR INTRAORAL SCANNER," and U.S. patent application Ser. No. 14/192,137 (now U.S. Pat. No. 10,111,581), filed Feb. 27, 2014, titled "THERMAL DEFOGGING SYSTEM AND METHOD," each of which is incorporated by reference herein in its entirety.

For example, described herein are removable barrier devices for covering a handheld intraoral scanner. A barrier device may include: a cover adapted to fit over a scanning portion of the intraoral scanner at a distal end of the scanner, the cover including a window for allowing transmission of an optical signal between the scanner and an external environment; wherein the cover is adapted to maintain the window in a fixed position relative to an optical component of the scanner; and a flexible sleeve extending from the cover and adapted to cover a handle of the scanner.

In general, the cover and the sleeve are made of one or more materials that is substantially impervious to contaminants.

In some variations the cover (or cover region/cover portion) and the flexible sleeve (or sleeve region are integrally formed as the same structure, which may be bag-like. Thus, both the cover and sleeve may be formed of a flexible material (e.g., as a plastic bag-like structure). The inside of the device may include an engagement region (e.g., within the cover region or cover portion) that is configured to removably engage with the distal end of the scanner and to secure the window in fixed relation to the scanner. For example, the engagement region may be a snap or friction-fit region including a projection that may engage with a contact or attachment on the outside of the distal end of the scanner, such as an elastomeric housing over the distal end of the scanner. Any appropriate engagement member (e.g., attachment, snap, friction fit, magnetic attachment, etc. may be used.

In some variations, the flexible sleeve may be coupled to the cover at an interface region configured to prevent fluid from passing through the barrier device between the cover and the sleeve. For example, the interface region may comprise an adhesive tape. In some variations the interface region comprises a gasket (e.g., an O-ring), which may be an elastomeric material. The gasket may be integral to the proximal cover. The gasket may be integral to the flexible sleeve. The gasket may be disposed over the proximal cover and the flexible sleeve to provide a compression fit.

In some variations, the interface region comprises a clip configured to releasably couple the cover and the sleeve. The device may include a gasket may seal the cover and sleeve together. The interface region may include a weld region that integrally couples the cover and the sleeve. The flexible sleeve may be more flexible than the cover.

Any of the devices described herein may include a nanostructured antireflective material on at least one side (e.g., both sides) of the window and configured to reduce internal reflections from the window.

Any of these devices may be held in a pre-deployed configuration. For example, the flexible sleeve may be held in a folded or compressed pre-deployed configuration within a packaging. The packaging may hold the flexible sleeve with the sleeve rolled up, folded or otherwise compressed so that the long channel through the sleeve remains open for insertion of the handle of the intraoral scanner, so that the sleeve may be unfurled (unrolled, unfolded, etc.) down over the handle and/or cord. This may advantageously prevent tangling and contamination or fouling of the cover.

The sleeve may be adapted to cover one or more actuators of the handle, the sleeve being sufficiently thin and flexible for a user to actuate the one or more actuators from an outer surface of the sleeve.

Any of these device may have a length from a distal end of the barrier device to a proximal end of the barrier device that ranges from about 6 to about 20 inches.

Any of these device may include an air flow director configured to direct air flow to and from the scanner, wherein the sleeve is configured to cover at least a portion of the air flow director. The airflow direction may include a channel, tube, etc.

The device may be single-use, or the device may be reusable (including sterilizable, e.g., autoclavable). For example, one or both of the cover and the sleeve may be made of an autoclavable material.

In some variations, the proximal cover may include two or more pieces configured to mechanically join together around the scanning portion of the intraoral scanner. For example, the two or more pieces may be configured to snap fit together.

Also described herein are methods of operating an intraoral scanner, the method comprising: scanning, using the intraoral scanner, an identifier of a sleeve, wherein the identifier is located on a sleeve; identifying, from a database, one or more characteristics specific to the sleeve based on the identifier; and adjusting the operation of the intraoral scanner based on the identified one or more characteristics.

The one or more characteristics may include information related to the optical characteristics of the window(s) of the sleeve (such as thickness, transparency, curvature, material properties, etc.). The one or more characteristics may include information about the sleeve (e.g., batch number, recalls, regional permission for use, etc.).

Any appropriate identifier may be included, such as a bar code, QR code, alphanumeric code, logos, or symbol, etc. The identifier may be on the inside or outside of the sleeve. In some variations the identifier is on the window of the sleeve.

The step of identifying from the database may include accessing a remote database and/or accessing a local database. In some variations the local database may be part of the apparatus. The remote and/or local databases may be maintained and/or updated to include new information about sleeves.

Adjusting the operation of the intraoral scanner may include adjusting one or more of: calibration parameters (include focal length, scanning rate, scanning intensity, wavelengths, etc.) and/or use modes of the intraoral scanner.

BRIEF DESCRIPTION OF THE DRAWINGS

Novel features of embodiments described herein are set forth with particularity in the appended claims. A better understanding of the features and advantages of the embodiments may be obtained by reference to the following detailed description that sets forth illustrative embodiments and the accompanying drawings.

FIG. 1C illustrates a view of another variation of an intraoral scanner with vents disposed on a proximal end of the scanner and not on the handle.

FIG. 1D is one example of a cable interface configured to connect to the intraoral scanner of FIG. 1C.

FIG. 1E is one example of a protective cover configured to seal the vents of the intraoral scanner of FIG. 1C.

FIGS. 2A-2L illustrate examples of barrier devices and components of barrier devices (e.g., barrier devices configured as a protective sleeve).

FIG. 2A is one example of a barrier device (protective sleeve) for an intraoral scanner including a semi-rigid or rigid distal end region and a thin and flexible proximal portion sealed to and extending from the distal end region.

FIGS. 2B and 2C illustrate the rigid or semi-rigid distal end portion of a protective sleeve (e.g., barrier device).

FIG. 2D1 is an exemplary schematic for a flexible proximal portion of a protective sleeve that may extend from a more rigid or semi-rigid distal end region, showing exemplary dimensions (that may be +/−5%, 10%, 15%, 10%, etc.).

FIG. 2D2 is an exemplary schematic of another variation of a proximal portion of a protective sleeve that may extend from a more rigid or semi-rigid distal end region, also showing exemplary dimensions (that may be +/−5%, 10%, 15%, 10%, etc.).

FIGS. 2E-2F4 illustrate one example of methods of attaching a flexible proximal portion of a protective sleeve to a more rigid distal end region, e.g., using an adhesive (such as an adhesive tape) or an elastomeric gasket (such as an O-ring).

FIG. 2G1 shows one example of an assembled protective sleeve including both a more rigid distal end region and a more flexible proximal end region having an opening support (e.g., paper backing) which may be released or left in place during use.

FIG. 2G2 shows another example of an assembled protective sleeve including both a rigid distal end region and a more flexible proximal end region packaged in a pre-deployed form, in which the flexible proximal end region is rolled or compressed so that it can be placed over the distal end of an intraoral scanner and deployed (e.g., by extending) over the intraoral scanner, as described herein.

FIGS. 2H-2I illustrate the application of a protective sleeve such as that shown above in FIG. 2G1 onto an intraoral scanner (e.g., a wand of an intraoral scanner), as described herein.

FIG. 2J illustrates another example of a protective sleeve in which a flexible proximal end region is coupled to the more rigid distal end region (e.g., the distal face of the distal end and/or a slightly more distal region on the outside of the more rigid distal end region) by, e.g., welding.

FIGS. 2K-2L illustrate perspective and top views, respectively, of another variation of a protective sleeve as described herein, in which the protective sleeve extends only partway down the handle region of the wand.

FIG. 6A illustrates a side view of the cover showing a distal portion and a proximal portion molded together.

FIG. 6B illustrates an aerial view showing a sleeve molded to the proximal portion of the cover.

FIG. 6C illustrates a top view of the cover; FIG. 6D illustrates a side view of the cover; and FIG. 6E illustrates a bottom view of the cover.

FIG. 6F illustrates another bottom view of the cover; and FIG. 6G illustrates a section view of FIG. 6F.

FIG. 6H illustrates a close up view showing a molding region of the distal portion of the cover; FIG. 6I illustrates a close up view showing a molding region of the proximal portion of the cover; and FIG. 6J illustrates the molded regions of the distal portion and the proximal portion of the cover.

FIG. 6K illustrates another close up view showing molding region of the distal portion of the cover.

FIG. 6L illustrates a drafting angle of the cover.

FIG. 8A illustrates a perspective view of the cover showing the separately formed window and adhesive.

FIG. 8B illustrates a top view of the cover and FIG. 8C illustrates a side section view of the cover.

FIG. 8D illustrates a perspective view of the cover and FIG. 8E illustrates another side section view of the cover.

DETAILED DESCRIPTION

Described herein are coverings providing a biological barrier to a medical device to prevent cross-contamination during use on patients. The barrier devices are well suited for covering optical scanners that are handled by practitioners (e.g., doctors, dentist, orthodontists, dental technicians, etc.) to obtain images of a patient's body. Any of the barrier devices described herein may be removable from the optical device so that the barrier devices can be easily replaced and/or cleaned between imaging operations. For example, the practitioner may install the barrier device on the optical device before imaging the patient's teeth, then remove the barrier device from the optical device after the imaging operation is complete. In some cases, the barrier device (or a portion of the barrier device) is disposable so that the practitioner can throw away the barrier device (or a portion of the barrier device) as medical waste after use. A new and clean barrier device can then be placed on the optical device for a subsequent imaging operation. In some cases, the barrier device (or a portion of the barrier device) is reusable so that the practitioner can properly clean the barrier device (or a portion of the barrier device) before reuse.

Figure 1A:
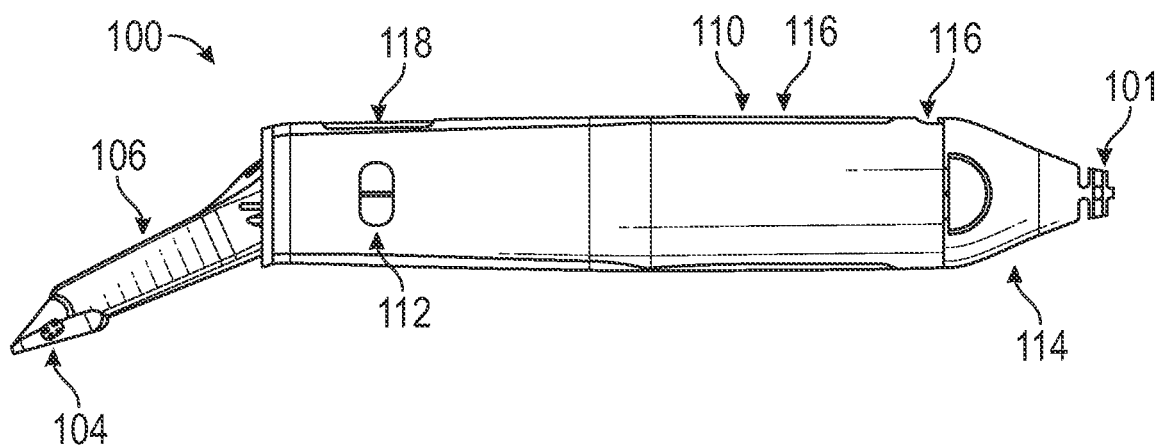
FIG. 1A shows a side view of one variation of an intraoral scanning device (intraoral scanner).

FIG. 1A shows an example scanning device 100 according to some embodiments. An enclosure of the scanner 100 can include internal optical components for taking images of the patient's dentition. The scanner 100 in FIG. 1A is configured as an intraoral scanner and may be a handheld scanner that a practitioner can hold and maneuver by hand. In some embodiments, the scanner 100 is connected to a power source and/or computer via one or more cables 101 (e.g., wires or cords). In some embodiments, the scanner 100 is configured to send data to a display that displays images of the patient's dentition collected by the scanner 100. In some cases, the scanner 100 is configured to take two-dimensional and/or three-dimensional images of the dentition. In some embodiments, the scanner 100 is has its own power supply (e.g., battery) and/or wirelessly communicates with a computer.

The enclosure of the scanner can include a main body 108 and a scanning portion 106, which includes one or more optical components 104 (e.g., optical window) that transmit optical signals to and/or from the internal optical components. The scanning portion 106 can have a shape and size adapted to maneuver around the patient's dentition and position the optical component 104 with respect to the patient's dentition. In some embodiments, the scanning portion 106 is at a distal end of the scanner 100 with the one or more optical component 104 at one side of the scanning portion 106. In some cases, at least part of the scanning portion 106 may enter into or come near the patient's mouth during a scanning operation. The scanning portion 106 can be connected to a main body 108 at a non-parallel angle to provide better access and maneuverability around the patient's dentition. The main body 108 can include a handle 110 that is sized and shaped for a practitioner to hold by hand. The main body 108 can include one or more actuators 112 (e.g., buttons, switches, touchpads and/or sliders) for activating one or more functions of the scanner 100. In some cases, the main body includes one or more vents 116 (e.g., openings) that allow airflow to and from a ventilation component in the internal chamber of the scanner 100 for cooling the internal components of the scanner 100. In some cases, a proximal end of the main body 108 tapers at cable interface region 114 that couples the cable 101 to the main body 108.

Figure 1B:
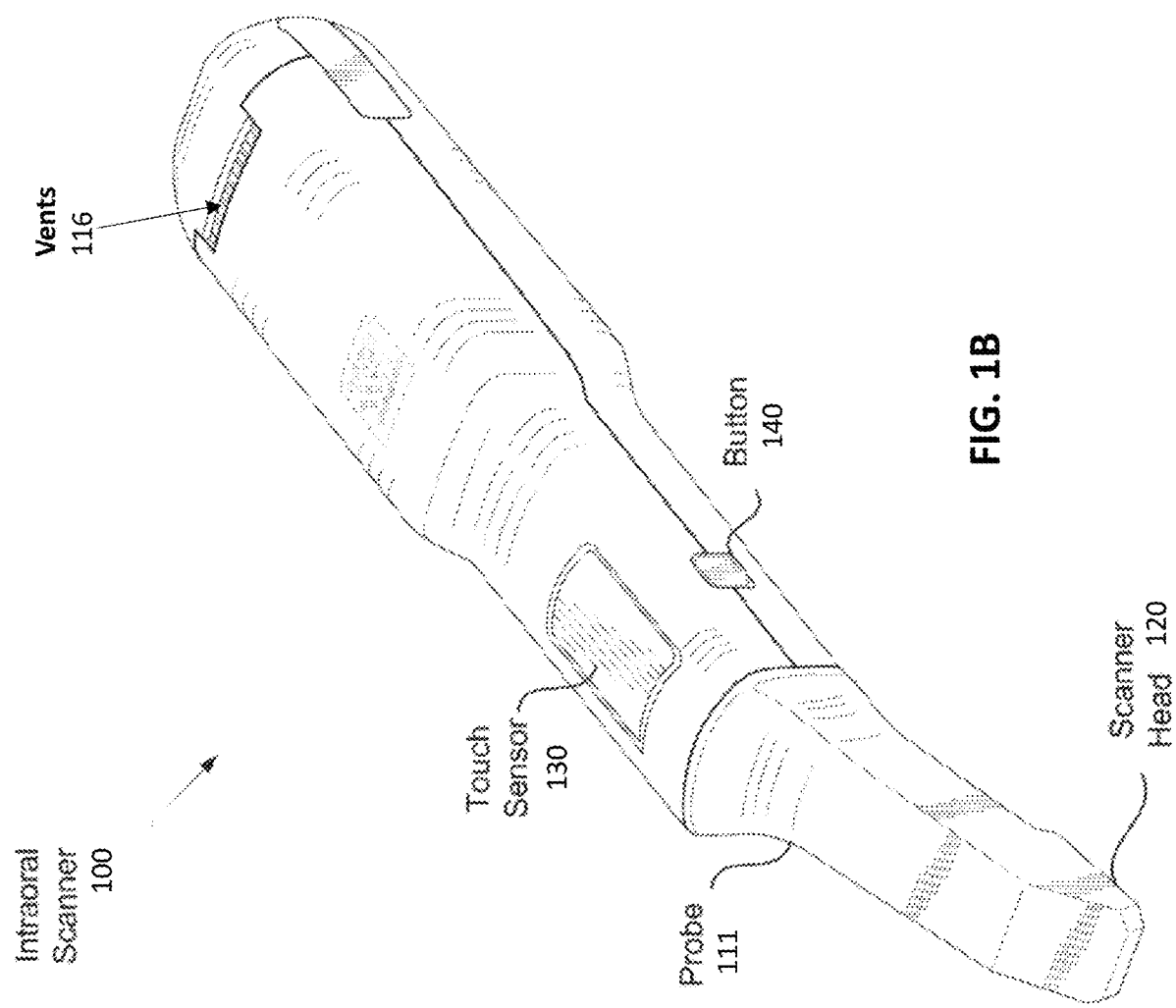
FIG. 1B illustrates a perspective view of another variation of an intraoral scanner with multiple inputs (e.g., a touch sensitive input, buttons, etc.) on the body of the wand.

FIG. 1B illustrates a perspective view of an intraoral scanner 100 that includes one or more inputs on the handle portion for controlling activity of the scanner. In this example, the scanner includes a touch sensitive input (e.g., touch sensor 130) and one or more buttons 140. The scanner may be a medical scanning device for scanning objects other than an intraoral cavity. Other types of medical scanning devices 100 to which embodiments of the present invention may apply include other types of optical scanners, x-ray devices, ultrasound devices, and so on. Each such medical scanning device may include at the least an image sensor to generate medical images, a communication module to transmit the medical images to a computing device, and a touch sensor usable to manipulate the medical images on the computing device and/or a representation of a scanned object generated from the medical images. These components may be coupled together directly or via a bus. The touch sensor may also be usable to navigate a user interface of a medical scan application running on the computing device. The medical scanning devices may additionally include one or more buttons that may be used both to initiate generation of the medical images and to activate and/or deactivate the touch sensor.

In one embodiment, intraoral scanner 100 may include a probe 111 that protrudes from one end of a body of the intraoral scanner 100. The probe 111 may include a scanner head 120 that captures optical data and provides the optical data to one or more optical sensors disposed within the intraoral scanner 100.

In one embodiment, intraoral scanner 100 includes a semiconductor laser unit that emits a focused light beam. The light beam may pass through an illumination module disposed within the intraoral scanner 100, which splits the light beam into an array of incident light beams. The illumination module may be, for example, a grating or a micro lens array that splits the light beam into an array of light beams. In one embodiment, the array of light beams is an array of telecentric light beams. Alternatively, the array of light beams may not be telecentric.

Intraoral scanner 100 may further include a unidirectional mirror or beam splitter (e.g., a polarizing beam splitter) that passes the array of light beams. A unidirectional mirror allows transfer of light from the semiconductor laser through to downstream optics, but reflects light travelling in the opposite direction. A polarizing beam splitter allows transfer of light beams having a particular polarization and reflects light beams having a different (e.g., opposite) polarization. In one embodiment, as a result of a structure of the unidirectional mirror or beam splitter, the array of light beams will yield a light annulus on an illuminated area of an imaged object within a field of view of the scanner head 120 as long as the area is not in focus. Moreover, the annulus will become a completely illuminated spot once in focus. This ensures that a difference between measured intensities of out-of-focus points and in-focus points will be larger.

Along an optical path of the array of light beams after the unidirectional mirror or beam splitter, intraoral scanner 100 may include confocal focusing optics, and probe 111 (also referred to as an endoscopic probing member). Additionally, a quarter wave plate may be disposed along the optical path after the unidirectional mirror or beam splitter to introduce a certain polarization to the array of light beams. In some embodiments this may ensure that reflected light beams will not be passed through the unidirectional mirror or beam splitter.

The probe 111 may internally include a rigid, light-transmitting medium, which may be a hollow object defining within it a light transmission path or an object made of a light transmitting material, e.g., a glass body or tube. In one embodiment, the probe 111 includes a prism such as a folding prism. At the end of the probe 111 where the scanner head 120 is located, the probe 111 may include a mirror of the kind ensuring a total internal reflection. Thus, the mirror may direct the array of light beams towards a teeth segment or other object. The scanner head 120 thus emits array of light beams, which impinge on to surfaces of scanned objects such as teeth.

The scanner 100 shown in FIGS. 1A-1B also includes one or more vents 116. The vents 116 can be, for example, inlet/outlet air vents configured to allow air flow into the device to prevent overheating during operation. In these examples, the vents 116 are generally located on a proximal portion of the handle 110 of the scanner. FIG. 1C illustrates another embodiment of an intraoral scanner 100 in which the vents 116 are not disposed on the handle 110, but instead are disposed on a proximal end (e.g., end face) 111 of the scanner 100 and/or routed through the cable interface 114. The advantage of moving the vents 116 to the proximal end (e.g., end face) of the scanner instead of being located on the handle 110 is that the vents, which provide an opening into the internals of the scanner, may be less likely to be contacted or handled by an operator during a scanning procedure. Since the proximal end of the device is unlikely to be touched during a procedure, sterilization of the device after a procedure can be simplified. For example, regulations may require that only portions of the device that contact a patient or an operator be sanitized after use. Thus, in the embodiment of FIG. 1C, the probe 106 and handle 110 portions of the scanner can be submerged or wiped down with a sterilization solution without the risk of sterilization solution entering the vents 116, which could potentially damage the scanner permanently. Referring still to FIG. 1C, the scanner may further include a number of seams 109 between the individual parts of the outer shell of the scanner. To further seal the scanner, these seams 109 may be additionally sealed, either internally or externally, with gaskets, O-rings, or silicon.

It should be noted that the scanner 100 of FIG. 1C can be powered with a hard-wired power cable, or can be implemented in a wireless version that includes a battery. The hard-wired version additionally requires a cable interface 114, as shown in FIG. 1D. In addition to providing electrical/data connections 113, the cable interface 114 can further include vent lumens 115 and exhaust vents 117, as shown. The vent lumens 115 may comprise male connections configured to mate/interface with the vents 116 of the scanner 100. Air flow into and out of the scanner 100 can be routed from vents 116 into vent lumens 115 and into/out of the exhaust vents 117 of the cable interface 114 during a procedure. The exhaust vents may be positioned more proximally (e.g., down the cable 133). For example, the cable may include one or more channels for exhaust and/or cooling that extend proximally to distally down the cable and may vent at a distance (e.g., 0.5 m or more, 0.7 m or more, 0.8 m or more, 0.9 m or more, 1 m or more, etc.) from the handle. In some embodiments, the vents 116, the vent lumens 115, and or the cable interface 114 itself may further include gaskets, O-rings, or other sealing mechanisms configured to prevent contaminants and/or liquids from entering the scanner.

FIG. 1E illustrates an embodiment of a protective cover 119 which is configured to be placed over the proximal end of the scanner when the scanner is not in use or when it is being sterilized. The protective cover 119 can include sealing plugs 121 which are configured to mate with the vents 116 to seal the vents and prevent contaminants or fluids from entering the scanner. In some embodiments, the sealing plugs 121 can comprise a soft, flexible material such as an elastomer or rubber. The protective cover 119 can further include an O-ring or gasket 123 disposed around a perimeter of the cover to further seal the vents of the scanner from contaminants or fluid when the cover is inserted on the scanner. With the protective cover in place, the scanner 100 of FIG. 1C can be fully submerged in a sterilization bath or wiped down with a high-level disinfectant without the risk of contaminants or fluids entering the scanner through the vents 116 or seams of the scanner. In some variations the wand, or a cover for use with the wand, may include valves that are configured to prevent ingress of fluid (e.g., sterilization fluid) into the wand apparatus when sterilizing. In some variations the valves may be disabled or otherwise opened during operation, e.g., by connecting a cable or power to the wand.

Described herein are barrier devices (e.g., protective sleeves) that typically include a rigid or semi-rigid distal portion that covers and/or forms the probe 111 portion of the scanner, and a more flexible, typically thinner, more proximal region that covers handle portion of the scanner, including any inputs (such as touch sensor 130 and/or buttons 140), typically without interfering with the activity of these inputs.

Figure 2A:
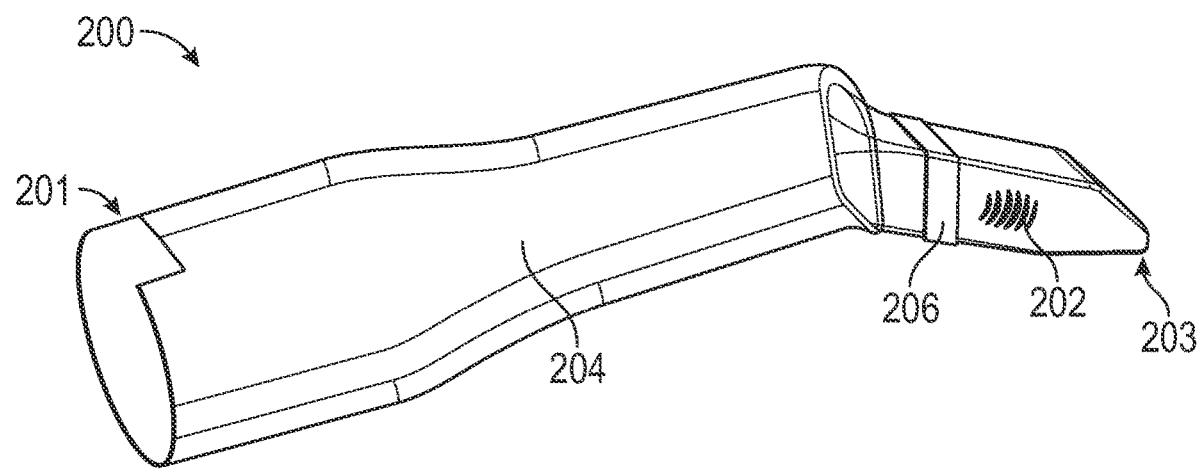

The barrier devices described herein can include aspects adapted to adequately cover surfaces of the optical devices while allowing proper functioning of various features of the optical devices. The barrier devices described herein can be adapted to cover some or all exterior surfaces of the scanning device. FIGS. 2A-2L show various components of an example barrier device 200 according to some embodiments. FIG. 2A shows the barrier device 200 fully assembled as it would cover a scanning device (e.g., 100, FIG. 1). The barrier device 200 in this example includes a distal rigid or semi-rigid portion (cover 202) adapted to cover at least part of a scanning portion/probe (e.g., 106, FIG. 1) of the scanner, a more flexible sleeve portion 204 (extending proximally from the more rigid portion) that is adapted to cover at least part of the handle (e.g., 110, FIG. 1), and an interface region 206 that connects and seals the distal more rigid portion (cover 202) to the proximal more flexible sleeve 204. The dimensions of the barrier device 200, and any of the barrier devices described herein, may vary depending on the dimensions of the scanner. The barrier device 200 is generally adapted to cover surfaces of the scanner that would be in contact with the patient, practitioner and any fluids from the patient and practitioner. For example, the barrier 200 may cover substantially all surfaces of the scanning portion (e.g., 106, FIG. 1) of the scanner that may otherwise come into contact the patient and/or the patient's body fluids. The barrier 200 should cover at least a portion of the handle (e.g., 110, FIG. 1) of the scanner that may otherwise be in contact with a practitioner's hand or glove. In some embodiments, the barrier 200 can have a length that extends proximally to at least the cable interface region (e.g., 114, FIG. 1) of the scanner. In some embodiments, the length of the barrier 200 from the distal end 203 to the proximal end 201 ranges from about 6 inches to about 20 inches (e.g., 6, 7.5, 9, 10.5, 13.75, or 19.5 inches). In some cases the cover 202 is reusable. For example, the cover 202 can be configured to allow it to be sterilized, e.g., by autoclaving or any other suitable method, between use.

Figure 2B:
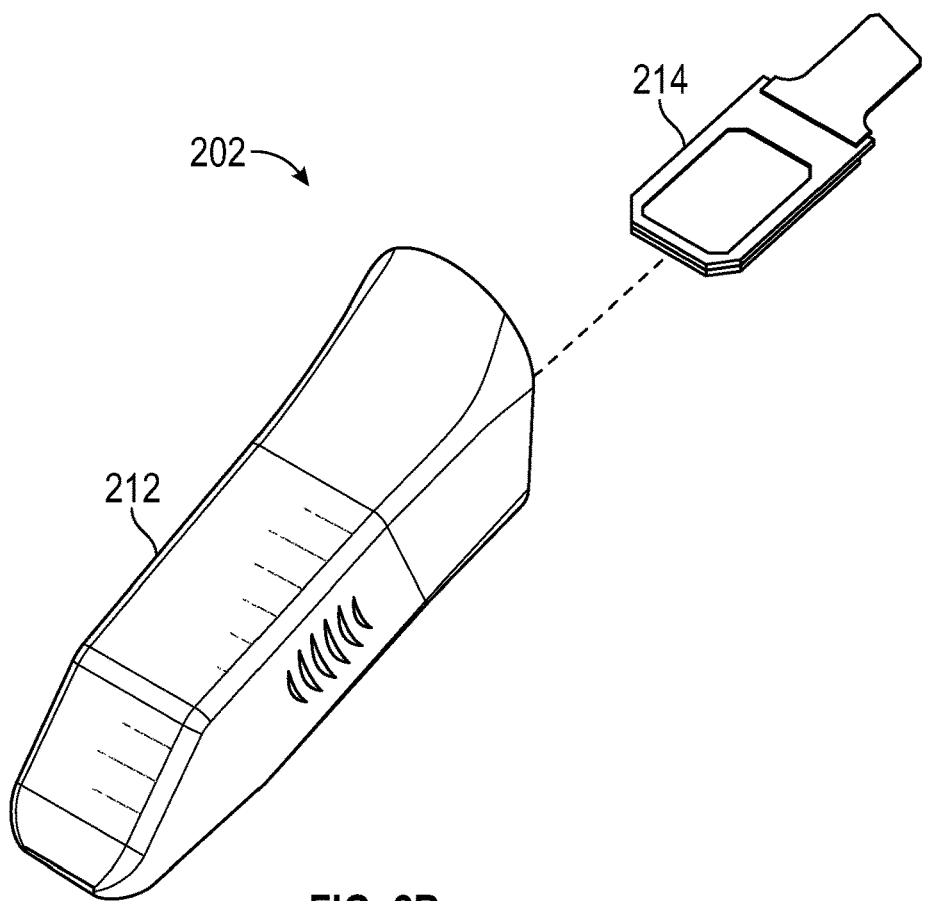
Figure 2C:
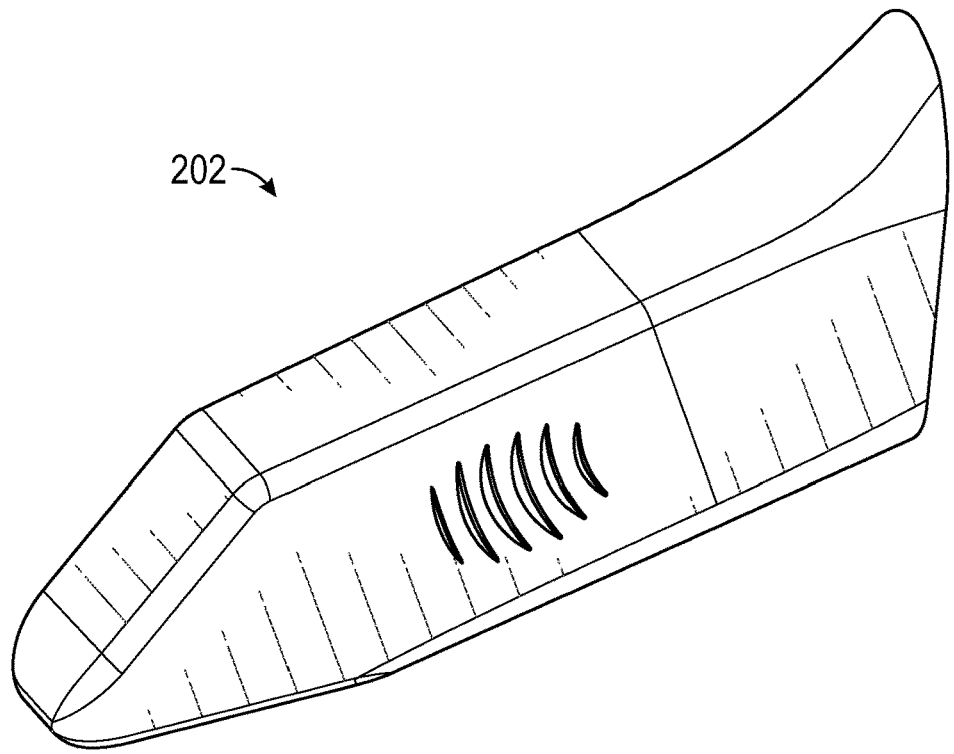

Referring to FIGS. 2B and 2C, the rigid or semi-rigid distal cover region 202 can include a body 212 that is shaped in accordance with the scanning portion (e.g., 106, FIG. 1) of the scanner. As described above, the scanning portion of the scanner is typically maneuvered around the patient's dentition. Thus, the body 212 should be light and non-bulky so as not to interfere with the maneuverability of the scanner. The walls of the body 212 can be made of a relatively rigid material so that the body 212 can maintain its shape. In some embodiments, the body 212 is made of a rigid polymer material, such as a polycarbonate material. In some examples, the body 212, and thus the distal cover region 202, can have an angular shape, such as a shape with square, triangular, or rectangular cross-sections. In other examples, the body 212 and distal cover region 202 can be cylindrical or have an elliptic cylindrical shape.

A window 214 can be positioned within an aperture of the body 212 to cover an optical component (e.g., 104, FIG. 1) of the scanner. The window 214 can provide a protective barrier for the scanner's window against gross contamination and physical damage. The window 214 can be made of an optically transparent material to allow transmission of an optical signal (e.g., light) to and/or from the scanner. In some embodiments, the window 214 is made of a glass, quartz, sapphire and/or an optically transparent polymer material. In some embodiments, the window 214 provides a calibration surface for the scanner. For example, the optical components of the scanner can calibrated to take into account the presence of the window 214. The body 212 may be adapted to maintain a position and orientation of the window 214 with respect to the optical component of the scanner, for example, during a scanning procedure. For example, one or more surfaces (e.g., walls, edges and/or retaining features) of the body 212 may engage with the scanner to maintain the window 214 in alignment with respect to the optical component (e.g., 104, FIG. 1). Further, the body 212 may position the window 214 to be a prescribed distance from the optical component of the scanner. The rigidity of the body 212 can provide physical protection and protection against gross contaminants for the scanning portion of the scanner, as well as ensure repeated and accurate placement of the window 214. It should be noted that although the body 212 shown in FIGS. 2B and 2C includes one window 214, the barrier devices describe herein can include any number of windows. For example, the barrier devices can include multiple windows in accordance with corresponding multiple optical components of a scanning device.

In variations in which the window 214 is formed separately from the body 212 and attached, the window 214 may be coupled to the body 212 in any appropriate manner, including with one or more of: adhesives, welding, flexible gaskets, and mechanical fastening.

Note that in some variations the sleeve may not include a separate, more rigid body portion 212, but may all be formed as a flexible sleeve (e.g., sleeve 204). Thus, in some variations the window may be directly attached to the flexible sleeve 204, e.g., by any appropriate manner, such as by welding, adhesion, or other methods. In this configuration, the window 214 may be aligned with the scanner based on one or more elements on and/or in the scanner itself, and may not require a sleeve or body portion to achieve alignment. For example, attaching a sleeve directly to a window to form the full-wand cover (without the need of a rigid sleeve) may be done, e.g., using a custom-molded silicone cover for the scanner, which the window may fit into, but can be done using a variety of soft materials and attachment methods.

FIGS. 2D1 and 2D2 show examples of the flexible proximal sleeve 204 of the barrier device 200. The sleeve 204 may be provided on a backing 228 (e.g., paper backing), and in some cases, enclosed within a pouch 230 that is removed before coupling the sleeve 204 to the cover 202. The sleeve 204 can be made of a thin sheet of flexible material, such as a flexible polymer. The material may be sufficiently flexible and/or thin for a user to be able to activate one or more actuators on the scanner when the sleeve 204 covers the scanner. The thickness of the sleeve 204 may vary depending on, for example, the type of material. In some cases, the sleeve 204 is made of a polyethylene material (e.g., PEF) having a thickness ranging from about 0.001 inches to about 0.01 inches (e.g., 0.001, 0.002, 0.004, 0.005, 0.007 or 0.01 inches). The sleeve 204 may be more flexible than the cover 202. In some embodiments, the sleeve 204 is made of a different material (e.g., different polymer type) than the cover 202. In some embodiments, the sleeve 204 is made of the same material (e.g., same polymer type) as the cover 202 but is thinner than the cover 202. In some embodiments, the sleeve 204 substantially conforms to the shape of the main body (e.g., 108, FIG. 1) of the scanner. The sleeve 204 can have a tubular shape having an internal opening for accommodating the main body of the scanner. The sleeve 204 can include a narrow section 226 and a wide section 224. The wide section 224 can have a width that is large enough to accommodate the width of the main body of the scanner. The narrow section 226 can be configured to engage with the cover 202 and can include an open end 222 where the cover 202 can be positioned through.

In FIGS. 2D1-2D2, the flexible proximal portion is configured as two flat pieces of material that are attached together to form a mitten or glove-like structure (e.g., attached, e.g., by welding, gluing, etc.) along the edges; one side could remain attached to a support backing, as shown.

In any of the variations described herein, the proximal mouth of the flexible proximal portion may be configured to be supported by a support such as a paper or secondary material that is stiffer than the material forming the main portion of the flexible proximal portion. As will be described in relation to FIGS. 2H and 2I, the proximal end of the flexible proximal portion may be attached to a more rigid material (e.g., a paper, such as an adhesive-backed paper, etc., a polymeric material, etc.) that may help hold the mouth of the protective sleeve open to allow ease of inserting/removing the intraoral scanner wand into the protective sleeve. In some variations this proximal mouth may be configured to permit airflow into/out of the intraoral scanner. Non-limiting examples of such configurations may include channels or passages through the protective sleeve or along the protective sleeve to vent, limiting the length of the protective sleeve in the proximal direction to prevent covering or otherwise obstructing the vents, etc.

Figure 2E:
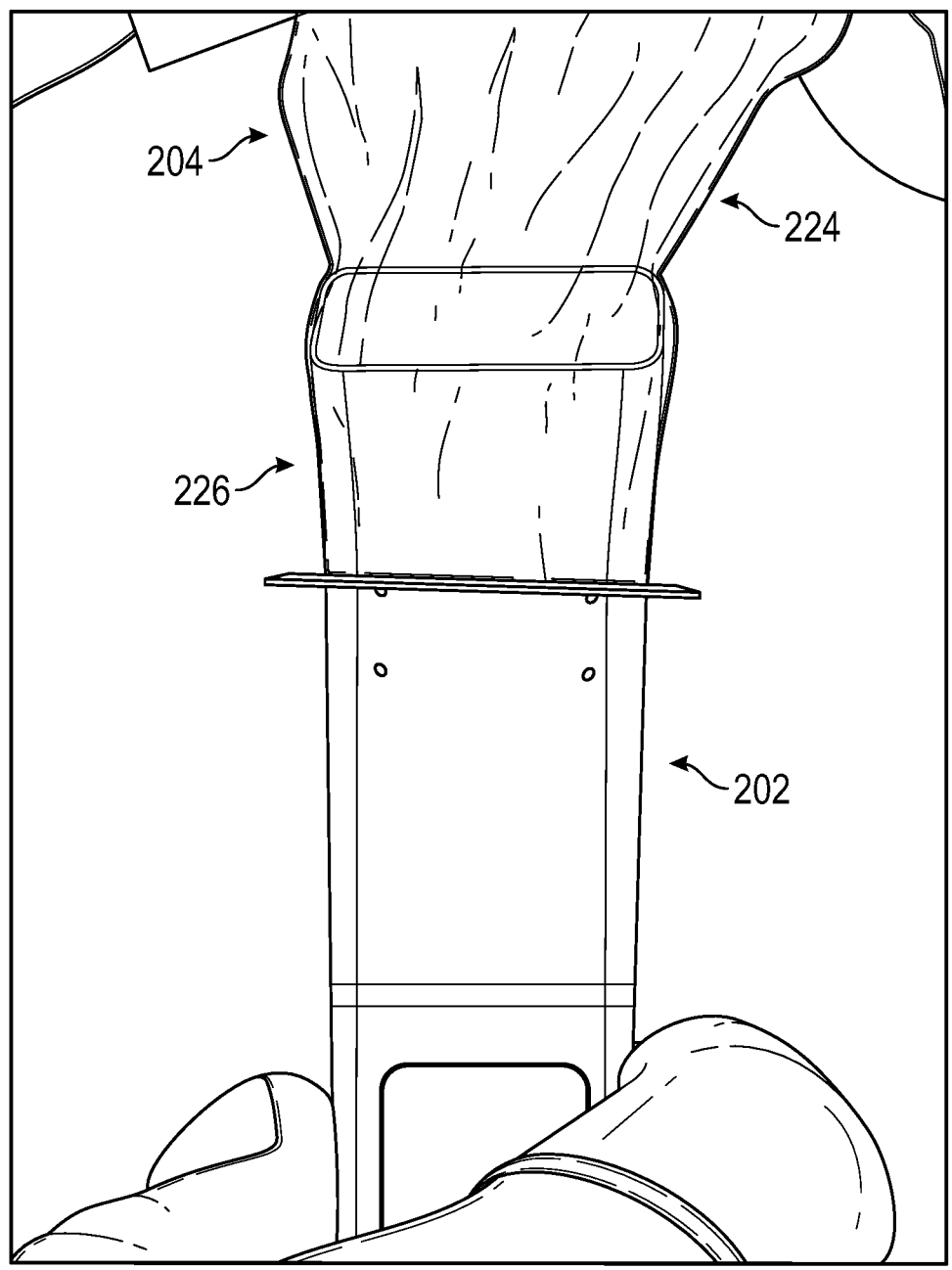

FIGS. 2E-2F4 illustrate one example of how a proximal, flexible portion of a sleeve 204 can be coupled to the more distal, more rigid cover 202 according to some embodiments. The distal more rigid cover 202 can be positioned partially through the opening of the narrow section 226 so that the narrow section 226 overlaps with the more flexible cover 202. The wide section 224 of the sleeve 204 can be left free for subsequent coverage over the scanning device.

FIG. 2F1 shows how an interface region 206 can be used to fixedly couple the sleeve 204 with the cover 202. The interface region 206 may be in the form of an adhesive tape that adheres the sleeve 204 to the cover 202. In some embodiments, about half of a width W of the tape covers the cover 202, and about half of the width W of the tape covers the narrow section 226 of the sleeve 204. In some embodiments, the tape is made of a polyethylene film having an acrylate adhesive. In some embodiments, the tape has a minimal width W for providing a proper seal (e.g., hermetic seal) between the cover 202 with the sleeve 204. In some embodiments, the minimum width W is about 20 mm.

In another embodiment, as shown in FIG. 2F2, the interface region 206 may be in the form of an elastomeric gasket that compresses and seals the sleeve 204 and the cover 202 to the scanner. The elastomeric gasket can comprise, for example, an O-ring, particularly in embodiments in which the cover 202 and body 212 have a cylindrical or elliptic cylindrical shape. In other embodiments, custom angular gaskets can be used to compress and seal the sleeve 204 against the cover 202 when the cover and body have angular shapes. The cover 202 can be placed over the sleeve 204 and compressed with the elastomeric gasket, or alternatively, the sleeve 204 can be placed over the cover 202 and compressed with the elastomeric gasket. In some embodiments, the elastomeric gasket is separate from the cover and sleeve. The elastomeric gasket can be configured to contact only the cover 202, only the sleeve 204, or can have a suitable width to allow the elastomeric gasket to span across the interface between the cover and sleeve to contact both components.

In other embodiments, as shown in FIGS. 2F3 and 2F4, the elastomeric gasket can be integrated with either the cover 202 or the sleeve 204. FIG. 2F3 illustrates an embodiment in which the gasket is integrated with the sleeve 204. In this example, the cover 202 can first be placed over the scanner and the sleeve 204 with the integrated interface region 206 can then be placed over the cover to compress and seal the cover and sleeve against the scanner. Alternatively, FIG. 2F4 illustrates an embodiment in which the interface region 206 in the form of an elastomeric gasket is integrated with the cover 202. In this example, the sleeve 204 can first be placed over the scanner, and then the cover 202 with the integrated gasket can be placed over the sleeve 204 to seal and compress the cover and sleeve against the scanner.

In some embodiments, the barrier device 200 is provided to a user (e.g., dental practitioner) in pre-assembled form so that the user only needs to insert the barrier device 200 onto the scanner. FIG. 2G1 shows the barrier device 200 as it may be presented to a user. The pre-assembled barrier device 200 can be provided in a packaging. For example, the cover 202 (e.g., rigid portion) may be covered in a bag 240 (e.g., polymer bag) and the sleeve 204 (e.g., flexible portion) may be provided on a backing 228 (e.g., paper backing). The sleeve 204 may be adhered to (e.g., welded to or coupled using adhesive) to the backing 228 such that the sleeve 204 is substantially flat and is extended along its full width.

Alternatively, in some variations, the sleeve assembly may be held in a pre-deployed form, in which the more flexible sleeve portion 204 is rolled, compressed, folded, etc. within the packaging 234 (which may hold it in the pre-deployed form, and/or may be held in the pre-deployed form by a releasable restraining member, such as a tie, wrap, etc.). As shown in FIG. 2G2, the assembly including the more rigid cover portion 202 and the flexible sleeve 204, which is "scrunched," is held in a bag 234. The user may place the cover portion 202 over the scanner, and pull the flexible sleeve portion 204 over the more proximal portion of the scanner to enclose the scanner and cabling of the scanner within the sleeve.

Figure 2H:
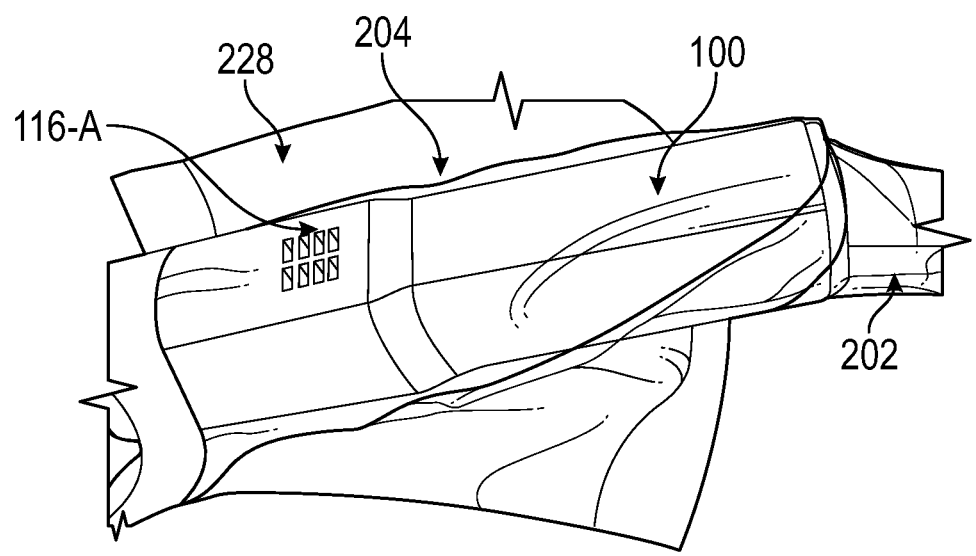
Figure 2I:
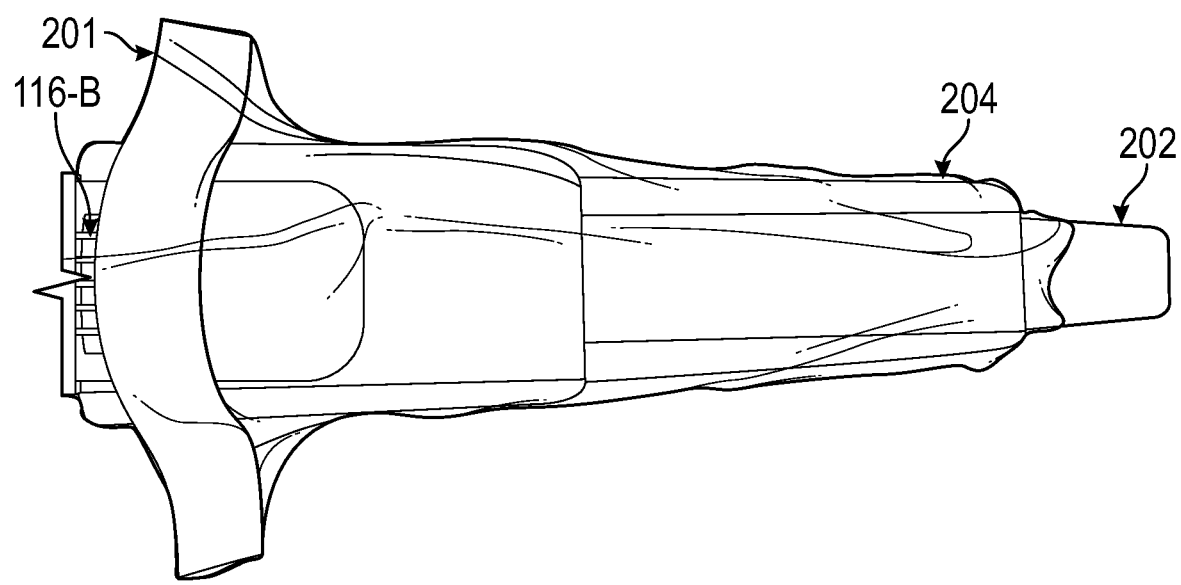
Figure 2J:
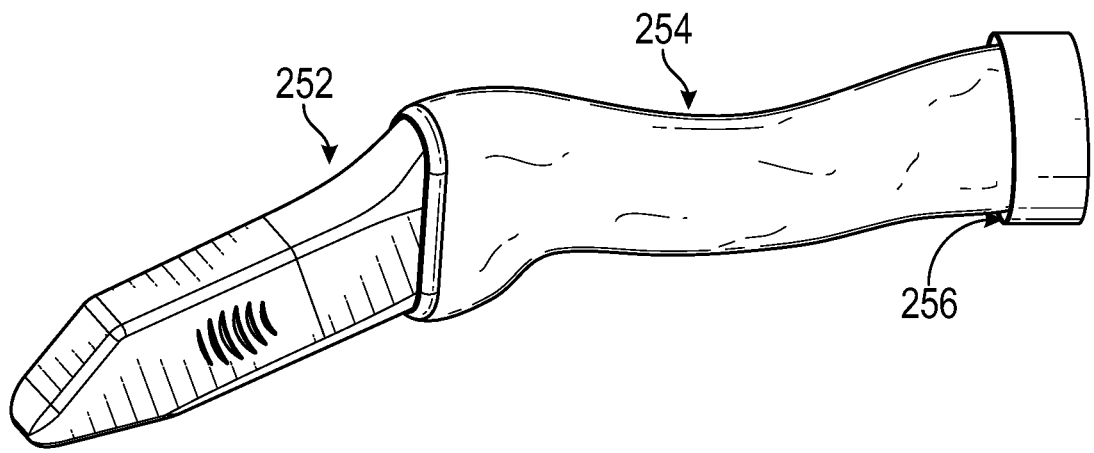

FIGS. 2H and 2I show views of the barrier device 200 being installed onto a scanner 100. The scanner 100 can be positioned through the sleeve 204 of the barrier device while still coupled to the backing 228. This can provide some stiffness to the sleeve 204 that allows the user to easily position the scanner 100 through the sleeve 204 such that the scanning portion of the scanner 100 can fully enter the cover 202 of the barrier device. The user can peel the backing 228 from the sleeve 204 after (or as) the barrier device is placed over the scanner 100. As installed, the sleeve 204 of the barrier device may loosely cover a first vent 116-A (e.g., inlet). At top of the proximal end of the sleeve 204 may stop short of a second vent 116-B (e.g., outlet) of the scanner 100. This can allow air to flow to and from the vents 116-A and 116-B of the scanner while the scanner is covered.

In some variations the protective sleeve may be formed of a more rigid distal region 252 to which a more flexible proximal portion 254 is attached, e.g., via an adhesive and/or welding. As mentioned above, the proximal portion 254 may be connected to a backing (not shown) and/or the proximal end may be supported to be easily opened and/or held open for inserting/removing the intraoral scanner and/or for permitting the scanner to be operated without occluding vents or preventing operation of the input controls (e.g., touchpad, buttons, etc.).

Figure 2K:
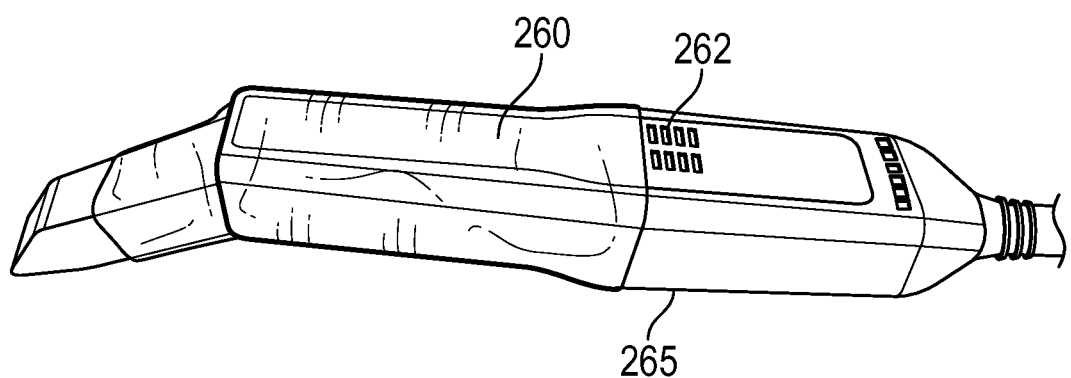
Figure 2L:
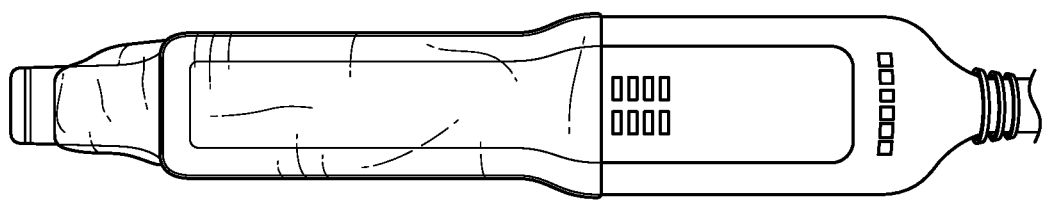

FIGS. 2K-2L illustrate another example of a protective sleeve that extends only partially down the length of the hand-held portion of a scanner. In FIGS. 2K and 2L the protective cover 260 extends partly down the handle portion 265, but does not cover the vents 262.

Figure 3A:
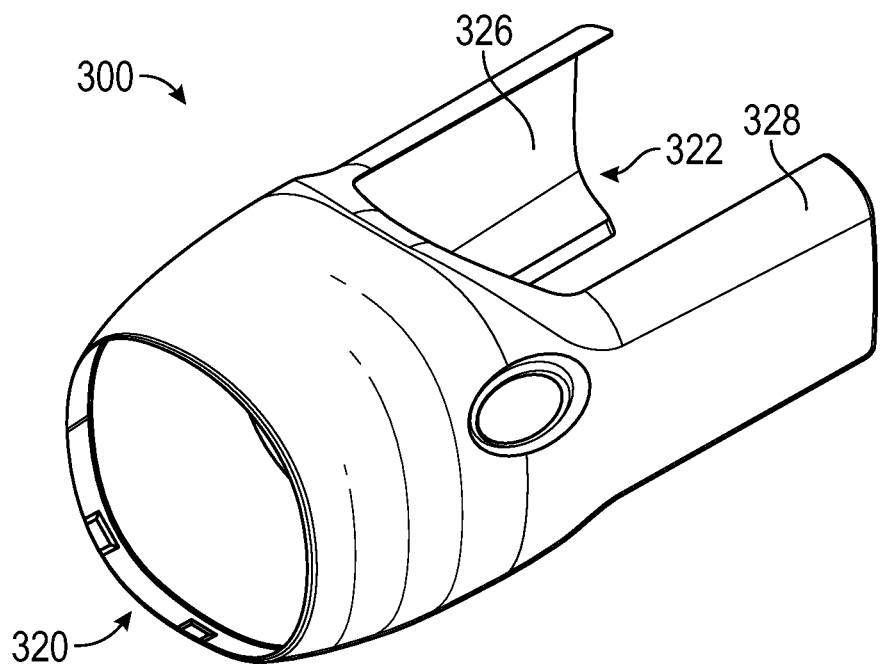
FIGS. 3A-3D show an example of an airflow director that may be used with an intraoral scanner and optionally with a barrier device.
Figure 3B:
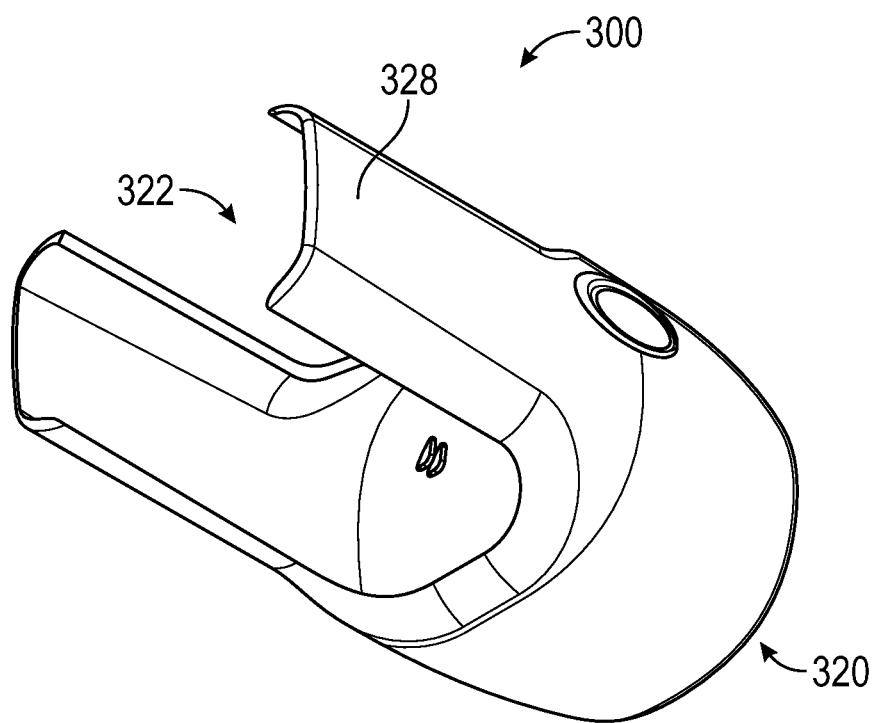
Figure 3C:
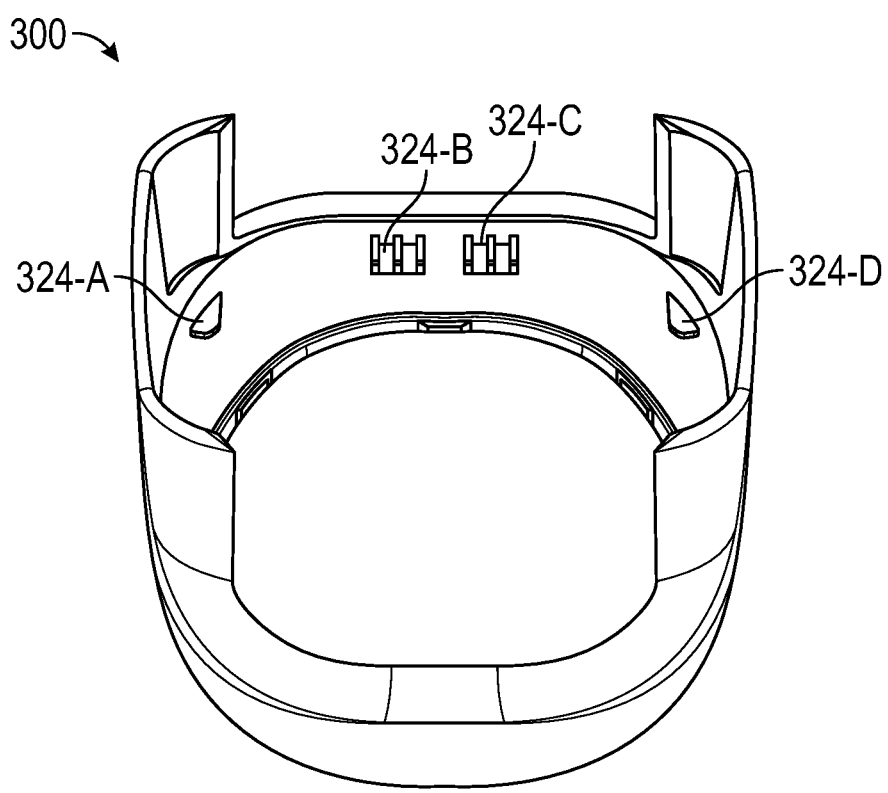

Referring to FIGS. 3A-3C, in some embodiments, the barrier device can be used with an airflow director 300, which is configured to direct the airflow to and/or from the scanner as part of the ventilation system of the scanner. The airflow director 300 can include a first opening 320 at a distal end and a second opening 322 at a proximal end. The second opening 322 may be in the form of a cutout that provides access to a top and/or bottom of the scanner. An interior surface 326 of the of the airflow director 300 can include one or more engagement features 324-A to 324-D, which are configured to engage with one or more surfaces of the scanner to keep the airflow director 300 coupled to the scanner, for example, during a scanning operation. The barrier device (e.g., 200, FIG. 2) can be configured to be placed over an exterior surface 328 of the airflow director 300.

Figure 3D:
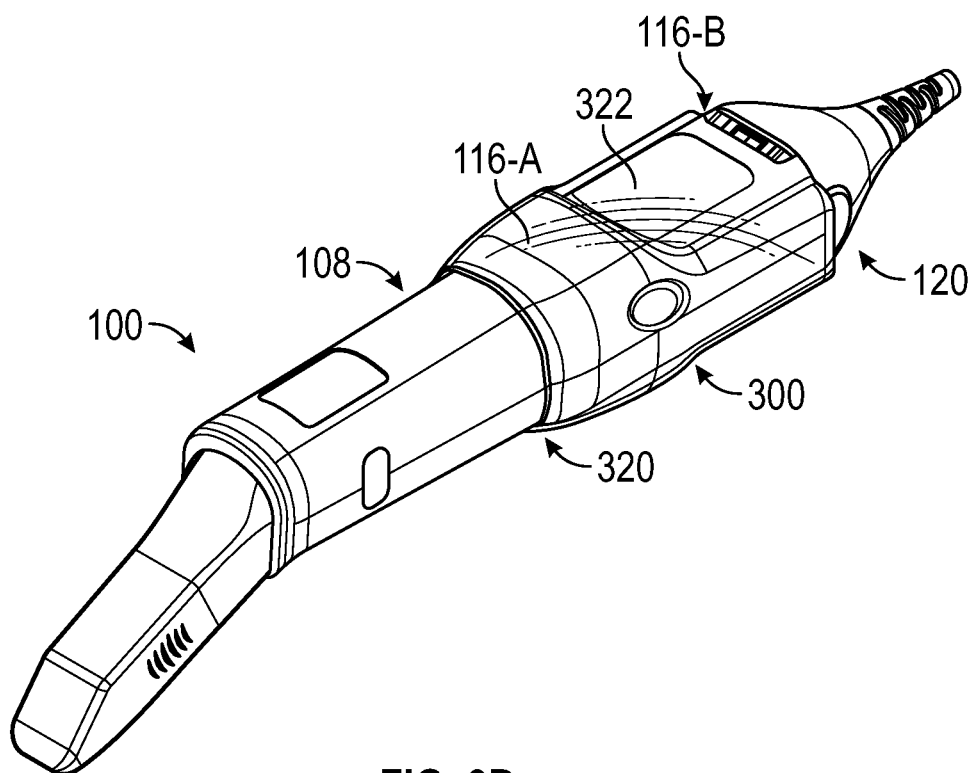

FIG. 3D shows the airflow director 300 assembled on a main body 108 of a scanner 100. The first opening 320 of the airflow director 300 can accommodate the main body 108 therethrough so that the airflow director 300 can encompass the main body 108. In some embodiments, the one or more engagement features 324-A to 324-D may engage with one or more surface of the main body 108 to keep the airflow director 300 coupled to the scanner 100. In some cases, the one or more engagement features 324-A to 324-D causes the airflow director 300 to click onto the scanner 100. In some embodiments, the engagement features 324-B and 324-C engage with one of the vents (e.g., 116-A) of the scanner 100. For example, the engagement features 324-B and 324-C can include protrusions that enter the openings of a vent. The second opening 322 can provide access to the vents 116-A and 116-B of the scanner. For example, the scanner 100 can include a first vent 116-A (e.g., inlet) and a second vent 116-B (e.g., outlet) for cooling the scanner 100. The airflow director 300 may hover over the first vent 116-A to provide a space between the airflow director 300 and the first vent 116-A, where air can enter (if vent 116-A is an inlet) or exit (if vent 116-A is an outlet) the scanner 100. The second opening 322 of the airflow director 300 can leave the second vent 116-B uncovered so that air can enter (if vent 116-B is an inlet) or exit (if vent 116-B is an outlet) the scanner 100. Thus, the airflow director 300 directs the airflow to and from the scanner toward the proximal end 120 of the scanner 100. Thus, when the sleeve (e.g., 204, FIG. 2A) of the barrier device is place over the airflow director 300, air can allowed to efficiently flow through the proximal opening (e.g., 201, FIG. 2A) of the barrier device.

Figure 4A:
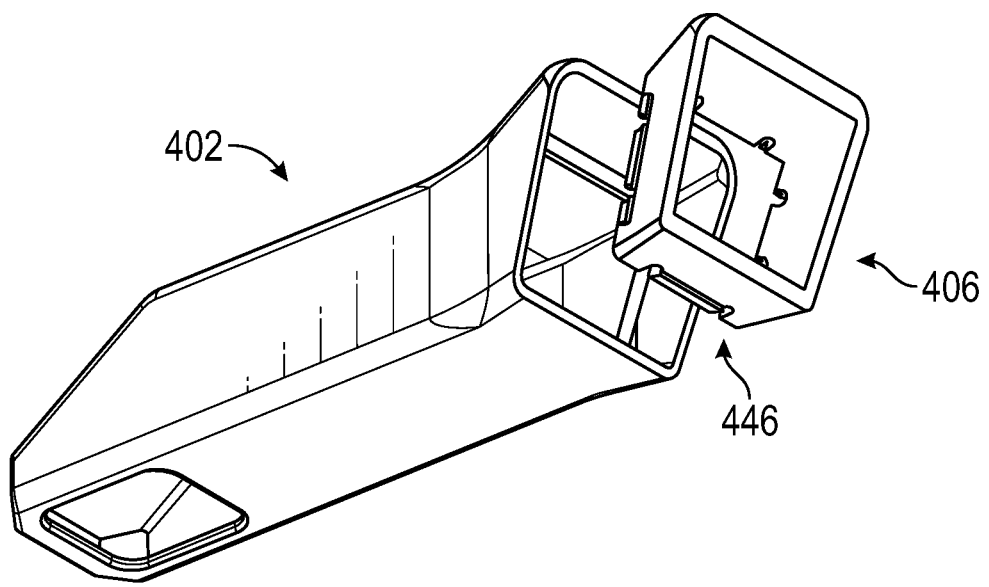
FIGS. 4A-4C show an example of another variation of a protective sleeve as described herein, including a releasable clip portion of a barrier device.
Figure 4B:
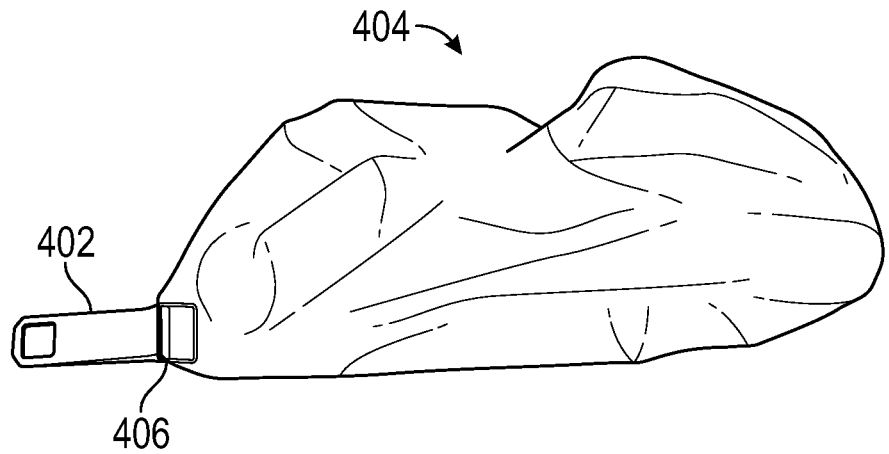
Figure 4C:
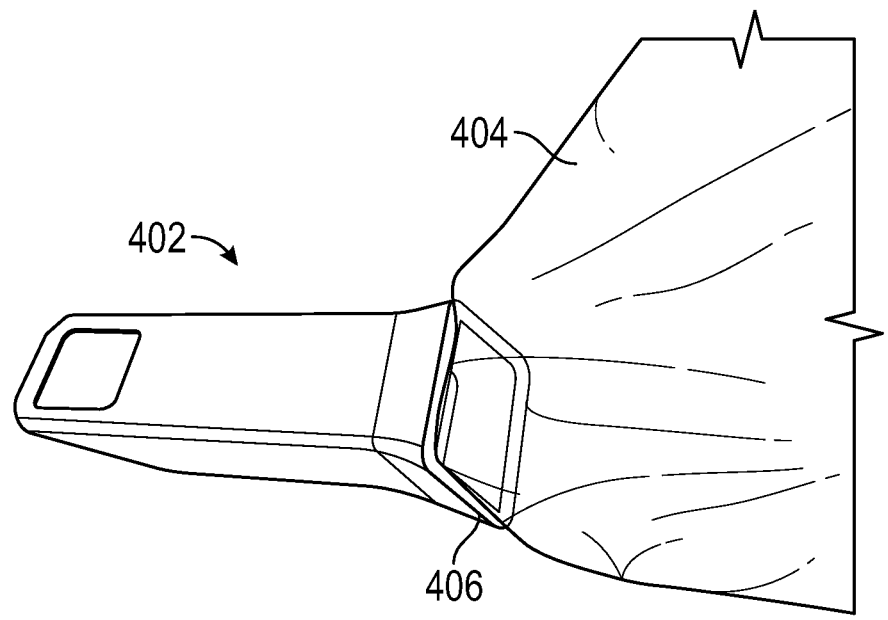

FIGS. 4A-4C show an alternative embodiment of a barrier device. In this embodiment, a cover 402 (e.g., rigid portion) of the barrier device is configured to removably couple with a retention clip 406. The retention clip 406 can be coupled to a flexible sleeve (e.g., 204, FIGS. 2A-2L) (e.g., flexible portion) of the barrier device. Thus, the retention clip 406 can replace the adhesive tape described above with reference to FIGS. 2A-2L. In some embodiments, a simple flexible bag is used instead of specifically sized sleeve (e.g., 204, FIGS. 2A-2L). The retention clip 406 can include engagement features 446 that are configured to removably engage with a proximal end of the cover 402. In some embodiments, the engagement features 446 includes a row of tabs positioned around a perimeter edge of the retention clip 406, and which engage with, for example, an edge of the cover 402 to form a snap fit between the two. In some cases, the retention clip 406 includes multiple rows of tabs to provide a more secure and tight seal between the parts. In some embodiments, the cover 402 and the retention clip 406 are made of the same material (e.g., polycarbonate). In some embodiments, the polycarbonate is a Polycarbonate/Acrylonitrile Butadiene Styrene (PC/ABS) material. In some embodiments, the cover 402 and the retention clip 406 are injection-molded from an optical grade polycarbonate. In some variations the device may also include a gasket in the interface between the cover body 402 and the retention clip 406 to ensure a seal between the rigid portion 402 and the flexible sleeve 404.

The releasable configuration of the retention clip 406 (e.g., as opposed to tape) may be useful when the cover 402 is reusable (e.g., autoclavable) and the sleeve is disposable. In particular, the retention clip 406 can allow a user to quickly couple and decouple the cover 402 from the sleeve between scanning operations. In some cases, the retention clip 406 is also reusable by removing the retention clip 406 from the disposable sleeve. FIGS. 4B and 4C show the cover 402 engaged with the retention clip 406, where the retention clip 406 is attached to a sleeve 404, which in this case is a simple flexible bag. In some cases, the sleeve 404 is inserted between the retention clip 406 and the cover 402 such that the sleeve 404 becomes coupled to the arrangement when the retention clip 406 is clipped to the cover 402. In this way, the sleeve 404 may help provide a tight seal between the retention clip 406 and the cover 402 (e.g., act effectively as an O-ring). In other embodiments, the retention clip 406 is fixedly coupled (e.g., by adhesive or molding) to the sleeve. In some embodiments, the sleeve 404 is a simple flexible bag that has a closed end that the user pierces with the retention clip 406 when attaching to the cover 402. In some cases, the retention clip 406 includes pry-apart features that can assist the user in separating the retention clip 406 from the cover 402.

Figure 5:
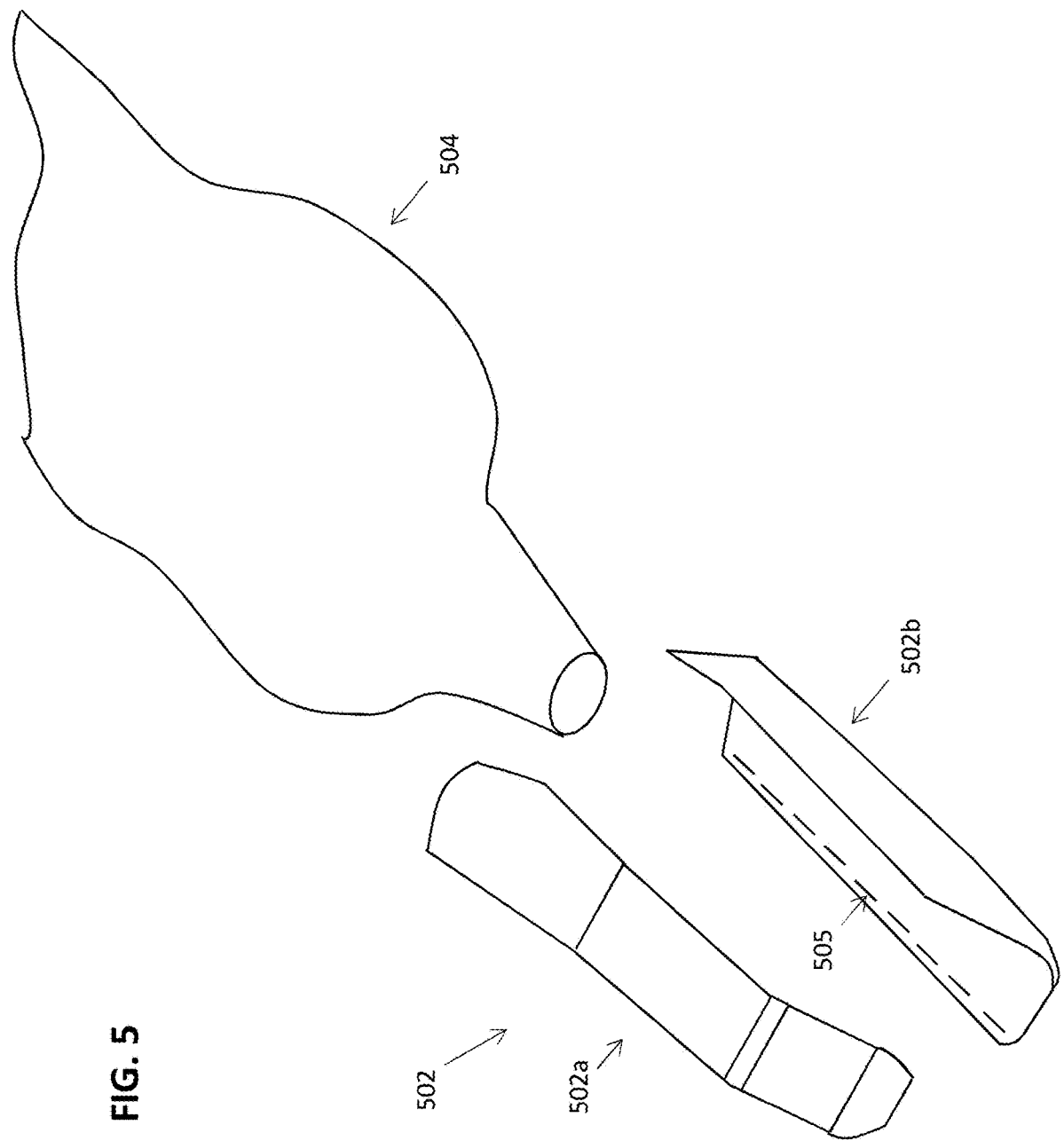
FIG. 5 illustrates another embodiment in which a cover comprises two or more pieces configured to mechanically join together around a sleeve and a scanner to provide a seal.

FIG. 5 illustrates another embodiment in which the cover 502 comprises two or more pieces 502a and 502b which are configured to mechanically join together around the sleeve 205 and scanner to provide a seal. In one embodiment, as shown, the cover pieces 502a and 502b can include interlocking components 505 on one or more surfaces of the cover pieces to allow the pieces to mechanically join together in a snap-fit manner. The interlocking components can comprise, for example, annular, cantilever, or torsional snap-fits. In one example, a sleeve 504 can be placed over the scanner, as described above. The cover 502 can then be mechanically joined (e.g., snap-fit) over both the scanner and the sleeve 504 to seal the scanner from contaminants. In some examples, an additional interface region such as tape or an elastomeric gasket can be provided between the cover and the sleeve, as described above, to provide an additional layer of sealing.

In some embodiments, the interface region connecting the cover and the sleeve is a welded region where the material of the cover is welded with the material of the sleeve. For example, a thermal process can be used to locally heat the material around the circumference of the cover and/or the sleeve until the two parts form an integral interface. In some cases, an ultrasonic welding process is used. In certain circumstances it may be preferable that the cover and the sleeve include the same type of material (e.g., same polymer) so that the welded region will have good integrity. For example, the cover and the sleeve may both be made of a polyethylene material (e.g., with the sleeve being thinner). In some circumstances it may be preferable that the cover and the sleeve include different types of material (e.g., different polymers) due to the benefits of these different material properties. For example, certain polymers are more rigid and therefore may be used to form the cover, while other polymers are more flexible and therefore may be used to form the sleeve. However, it may be difficult to weld different types of material together in a way that forms sufficiently strong bond.

The barrier devices described herein may be fully disposable or, alternatively, be fully reusable. In some cases, the barrier devices are partially disposable and/or partially reusable. For example, in some cases a barrier device is designed to be fully disposable so that the user can dispose of the barrier device after use (e.g., as medical waste). In other cases, the entire barrier device is designed to be sanitized (e.g., autoclavable) so that the barrier device can be reused. In some cases, portions of the barrier devices are disposable and other portions of the barrier devices are designed to be reusable. For example, in some cases the cover may be made of a material that is made of a material that is autoclavable (e.g., can withstand the heat of autoclave process) while the sleeve is made of a material that is not substantially autoclavable. In other cases, the sleeve is reusable and the cover is disposable.

In some variations, the barrier devices described herein are configured to be disinfected and reused. For example, in some variations the barrier device is configured or adapted to be disinfected by the use of a liquid disinfectant. The barrier device may be configured to be configured to be disinfected (or sterilized) removed from a wand, then replaced onto the same or a different wand. Alternatively or additionally, in some variations the barrier is configured to be disinfected while on (or forming a part of) the wand. Thus, the barriers described herein may be durable barriers that are configured to form a part of the wand that is reusable and can be disinfected without damage to the wand including the internal electronics and/or optics. In some variations the barrier is configured to be worn on the wand (or coupled to, integrated with or otherwise part of the wand) and disinfected by immersion into a disinfecting solution. Thus, the apparatuses described herein may be configured so that egress into/out of the wand is limited, e.g., by one or more valves or covers, that prevents fluid (including contaminants and/or disinfecting fluid) from entering the vents or other possible openings of the wand.

Any of the barrier devices described herein can be tested for effectiveness for acting as a biological barrier (e.g., bacterial and/or viral barrier). The tests may be in accordance with Good Laboratory Practice (GLP) and/or Good Manufacturing Practice (GMP) regulations per governmental agencies (e.g., FDA). In some examples, testing procedures include a submersion testing where the covered scanner is submerged in a broth with pathogen. The covered scanner is then removed from the broth and the barrier assembly removed from the scanner. The scanner is then tested to check that no pathogens have crossed the barrier, either through the material of either the cover and/or sleeve, or through the interface between the cover and sleeve.

In some examples, the testing is conducted on the barrier device without the scanner. Such testing procedures can involve exposing the barrier device to a test solution and inspecting the barrier device for evidence of passage of the test solution through the barrier device. In some cases, a portion of the barrier device that is most likely to allow ingress of biological material is tested, such as the interface(s) between the cover and sleeve, and/or other interface or sealing regions of the sleeve. One testing procedure involves exposing an outer surface of the barrier device to a solution containing a biological material (e.g., bacteria) and extracting samples from the opposing inside surface of the barrier device. The samples are then analyzed for evidence of the biological material. Another testing procedure involves exposing the barrier device to a non-biological solution as a proxy for a biological material solution. In one implementation, a synthetic blood is used. For example, the outer surface of the barrier device is exposed to the synthetic blood, then samples are extracted from the inner surface and analyzed for evidence of the synthetic blood. In some cases, the barrier device is tested for its ability to withstand water leakage. In one testing procedure, the inside of the barrier device is filled with water. The outside surfaces of barrier device are then inspected for evidence of water leakage after a predetermined time (e.g., between about 5 and 20 minutes). Results from both the non-biological solution tests and the biological material solution tests have shown excellent results.

Also described herein are sterilizing/disinfecting kits that may be used with any of the apparatuses (e.g., barriers, wands including a barrier, etc.) described herein. For example, a wand including a barrier may be sterilized by immersion sterilization into a bath or chamber that includes a holder configured to secure the wand outside of the immersion fluid at the proximal end, to prevent fluid from entering into the vents or other openings. In some variations the sterilization bath or chamber may be configured to both hold the wand over the sterilization fluid sufficiently long to ensure sterilization and also without exposing the vents of other regions of ingress to the sterilization fluid. In some variations the vent(s) on the wand are configured to be sealed or at least covered when seated in the sterilization bath, even if this portion of the wand (or wand an barrier) are not immersed into the sterilization bath or chamber.

Figure 6A:
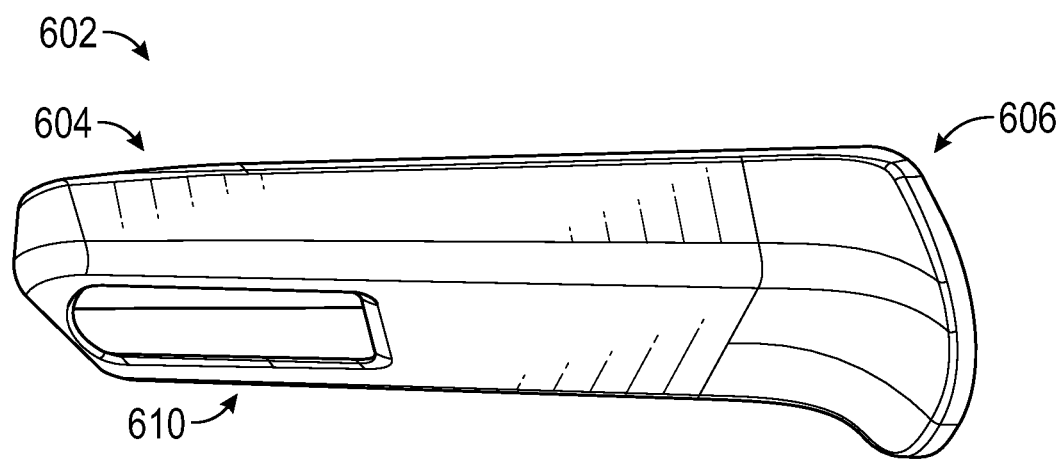
FIGS. 6A-6L illustrate another embodiment of a barrier device in which a cover of the barrier device comprises multiple molded portions to provide enhanced welding with a sleeve.

According to some embodiments, the cover of the barrier device includes multiple materials having different material properties for accomplishing different functions. FIGS. 6A-6L show an example barrier device made of different materials. FIG. 6A shows a cover 602 of the barrier device, which includes a distal portion 604 made of a first material and a proximal portion 606 made of a second material different than the first material. In this example, the distal portion 604 of the cover can include an optically transparent window 610 to allow transmission of optical signals to and/or from the probe of the scanning device. In this example, the window is made of the same material as the walls of the distal portion. Thus, the first material of the distal portion can be an optically transparent material. The walls of the distal portion can be sufficiently rigid to provide an internal cavity where the probe of the scanner will be placed. Thus, the first material can be sufficiently rigid to maintain the shape of the walls. According to some embodiments, the first material of the distal portion 604 may be a moldable polymer material (e.g., thermoplastic) that is sufficiently transparent to allow the scanner to transmit and/or receive optical signals. In some embodiments, the first material is a polycarbonate, a polymethyl methacrylate, Polyamide, Polymethylpentene, and/or other materials. The proximal portion 606 of the cover can be configured to bond to the distal portion 602 to create a seal (e.g., hermetic seal) between the distal and proximal portions. The bonding process may include forming a mechanical and/or chemical bond between the distal and proximal portions. In some embodiments, the proximal and distal portions are molded together via an injection molding overmolding process. In some cases, the second material may not be as optically transparent and/or as rigid as the first material of the distal portion of the cover. In some embodiments, the second material is a thermoplastic elastomer (TPE) material, such as Polyurethane, Polypropylene, Polyamide and/or other materials. According to some embodiments, the first and/or second materials are non-toxic (e.g., food grade or better) and have a flammability standard of UL 94 V2 or higher.

Figure 6B:
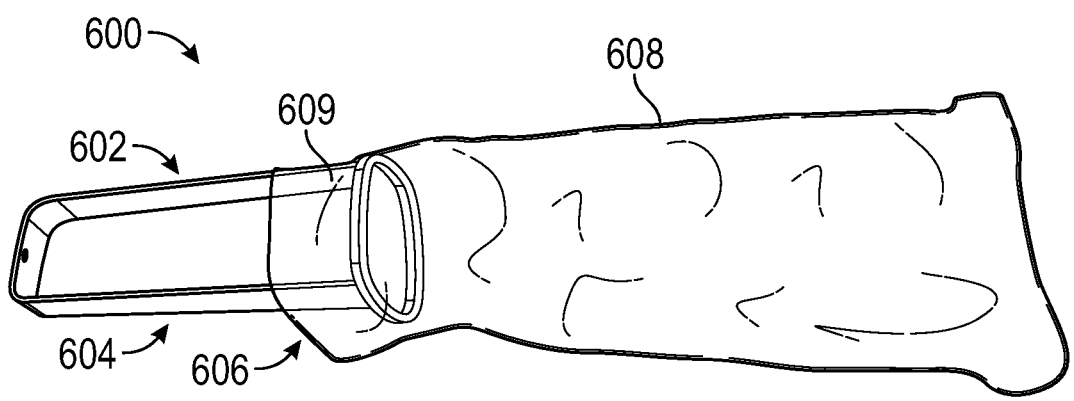

FIG. 6B shows a sleeve 608 bonded to the proximal portion 606 of the cover 602 at a bonding region 609 to create a seal (e.g., hermetic seal) between the sleeve and the cover. For example, a molding process or welding process can be used to bond the sleeve to the cover. In some embodiments, a heating process is used to heat the sleeve and/or the proximal portion of the cover to weld the pieces together. The bonding process may include forming a mechanical and/or chemical bond between the distal and proximal portions. Thus, the second material of the proximal portion 606 can be a material that is bondable (e.g., moldable or weldable) to the sleeve 608 and that is bondable (e.g., moldable or weldable) to the distal portion 604. According to some embodiments, the material of the sleeve is a medical grade plastic.

Figure 6E:
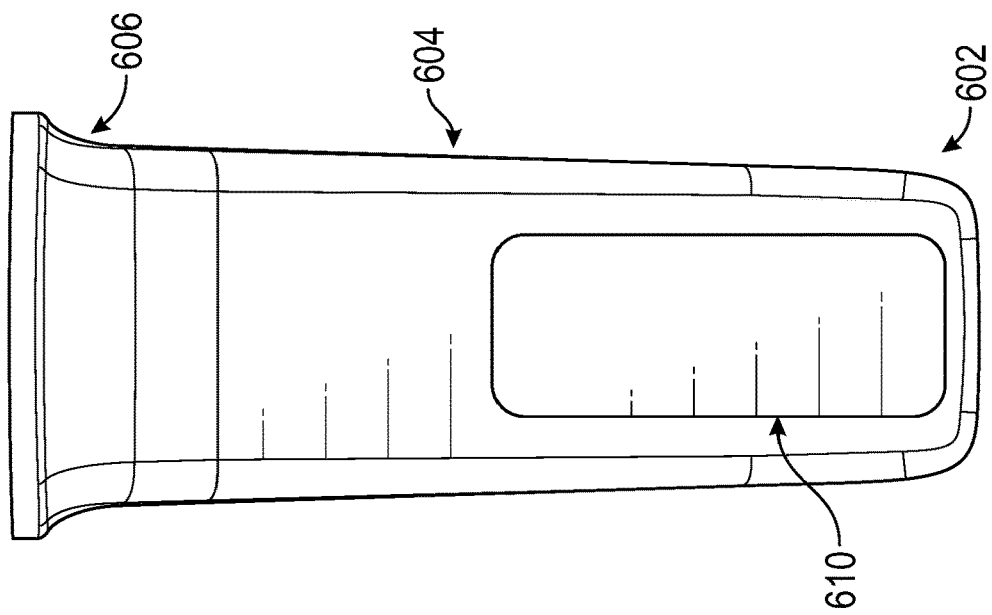
Figure 6D:
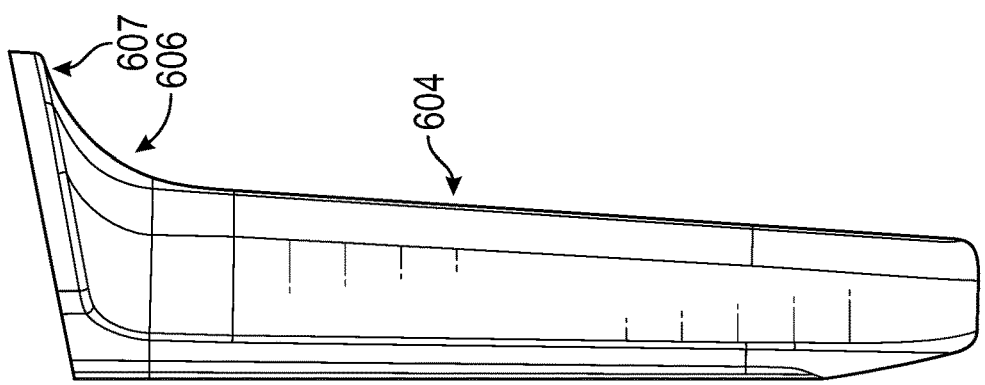
Figure 6C:
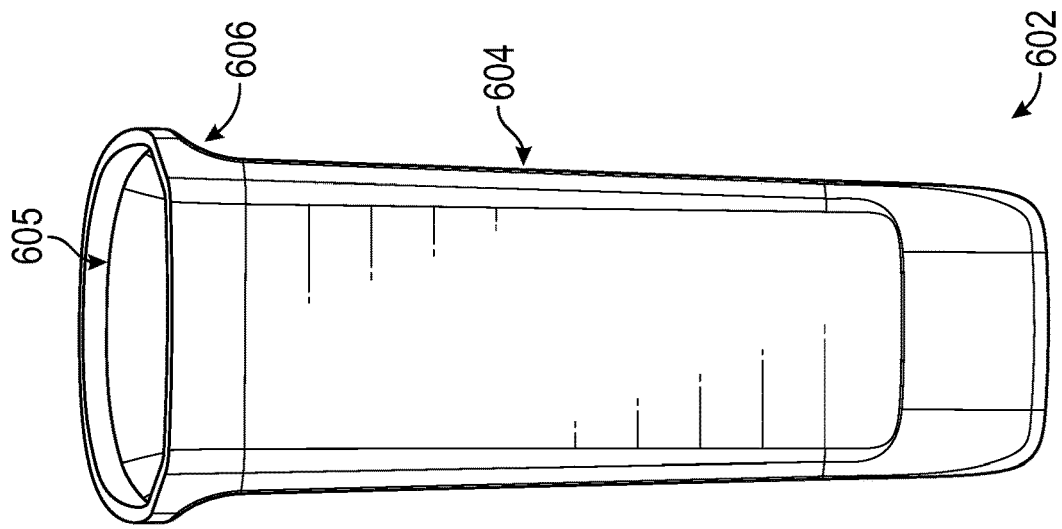

FIGS. 6C-6E show a top, side and bottom view, respectively, of the cover 602 of FIGS. 6A and 6B. The cover can be shaped to fit over the probe of the scanner. For instance, the cover can have an elongate shape in accordance with the probe, and include an opening 605 that provides access to an internal cavity where the probe resides. In some embodiments, the proximal portion 606 can be flared to fit with a corresponding flared portion of the probe. The proximal portion may include a lip 607 for engaging with the probe or other portion of the scanner. In some cases, the cover may slightly taper toward the distal end of the distal portion 604. The window 610 of the distal portion 604 can be shaped and sized to allow the optical components of the probe/scanner to transmit light between the probe and an external environment.

Figure 6G:
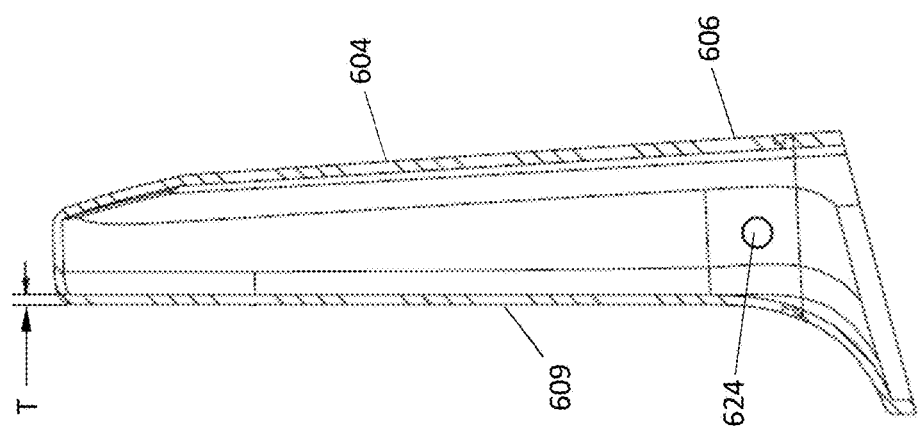
Figure 6F:
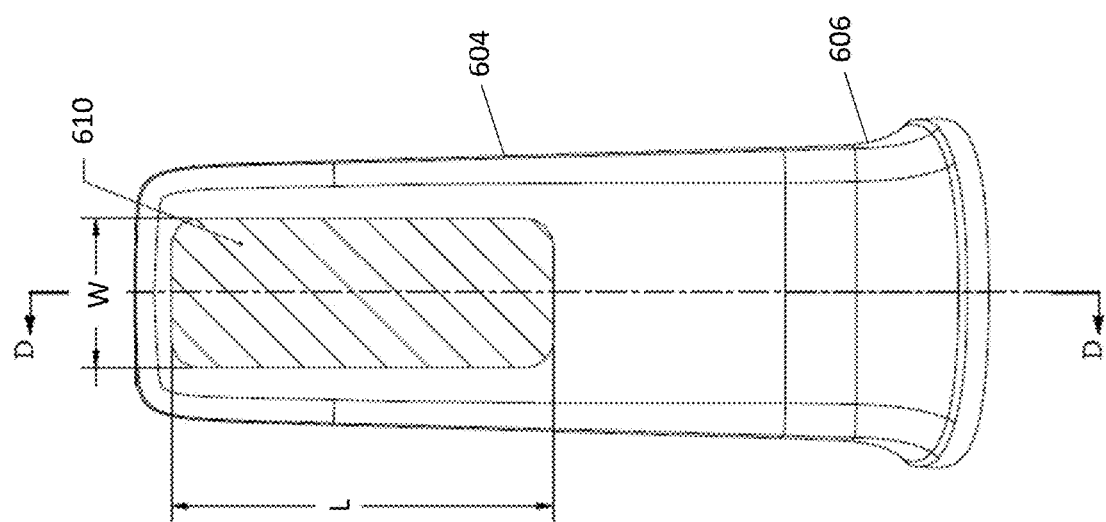

FIGS. 6F and 6G show a bottom view and section view D-D of the cover 602. The length L and width W of the window 610 may vary depending on the optical design of the scanning probe. In some embodiments, the length L of the window ranges from about 20 millimeters (mm) to 60 mm and the width W ranges from about 10 mm to 20 mm. The cover 602 may and have a low profile (e.g., thickness) so that the cover does not interfere with a scanning of a patient's dentition. In some embodiments, the window 610 (and/or one or more walls 609 of the cover) can have a thickness T ranging from about 0.5 mm and 3 mm (e.g., 0.5, 1, 1.25, 1.5, 2, 2.25, 2.5 or 3 mm). The window can have a uniform thickness in order to provide consistent transmission of the optical signal. In some embodiments, the thickness T of the window varies by no more than 0.5% to 3% (e.g., 0.5, 1, 1.5, 2, 2.5 or 3%). The material of the window (e.g., first material) can be configured to provide optimal transmission of light while still providing an effective pathogen barrier. In some embodiments, the window has refractive index ranging from 1.4 and 1.8 (e.g., 1.4, 1.45, 1.48, 1.5, 1.52, 1.55, 1.58, 1.6, 1.7 or 1.8). In one implementation, the material of the window (e.g., first material) may be configured to transmit wavelengths of light ranging from about 410 to 890 nanometers (nm). In some cases, the window material (e.g., first material) has a haze measurement of 6% (e.g., 6, 5, 4, 3, 2 or 1%) or less. In some embodiments, the distal portion (e.g., at least the one or more windows) has polished surfaces (e.g., external and/or internal surfaces) that are free of marks (e.g., gates, flashes, ejection marks, sink marks, welding marks, porosities, scratches sand blemishes). In some cases, the internal surface and/or the external surface of the window is polished to have a scratch-dig specifications of 40-20. In some implementations, the internal surface of the distal portion 604 and/or the proximal portion 606 includes one or more securing features 624, which may include one or more recessed or protruding features configured to engage with a corresponding recessed/protruding feature of the probe to secure the cover to the probe.

Figure 6H:
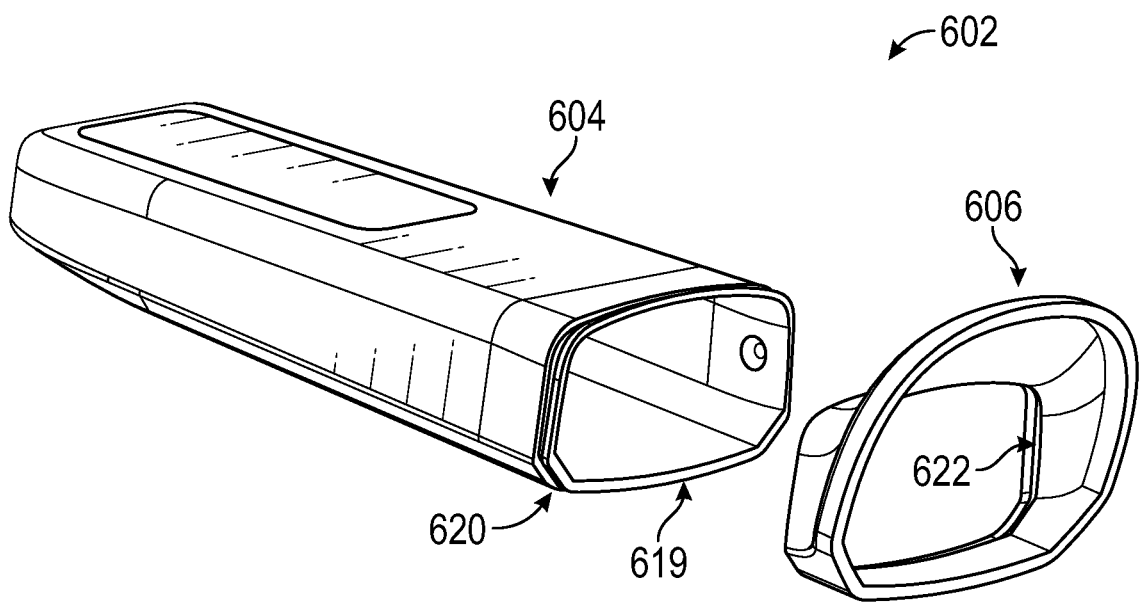
Figure 6I:
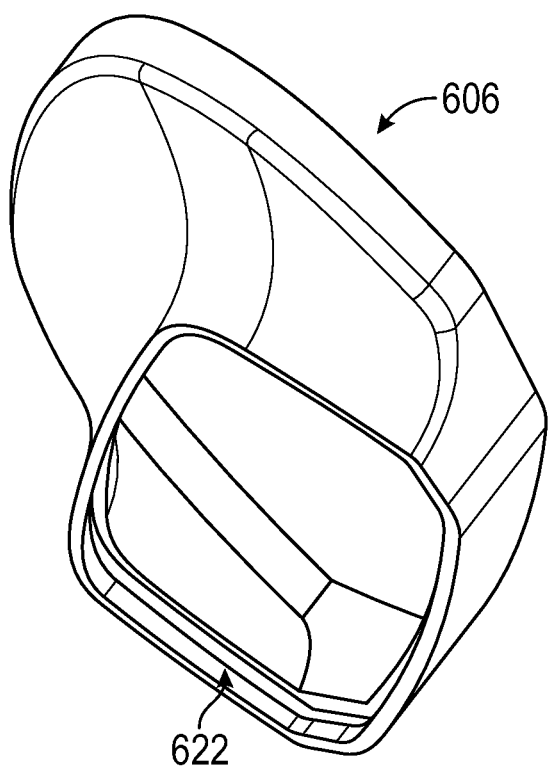
Figure 6J:
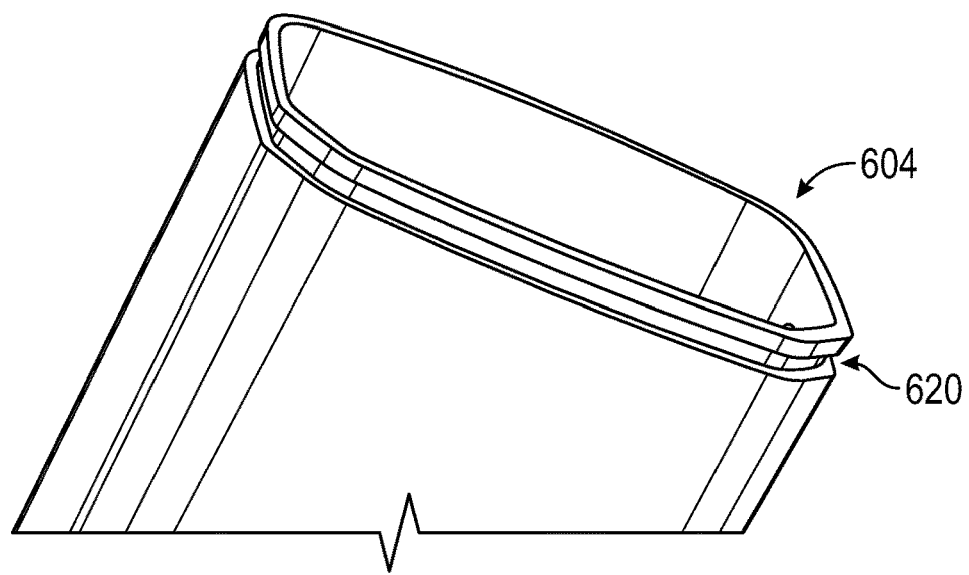
Figure 6K:
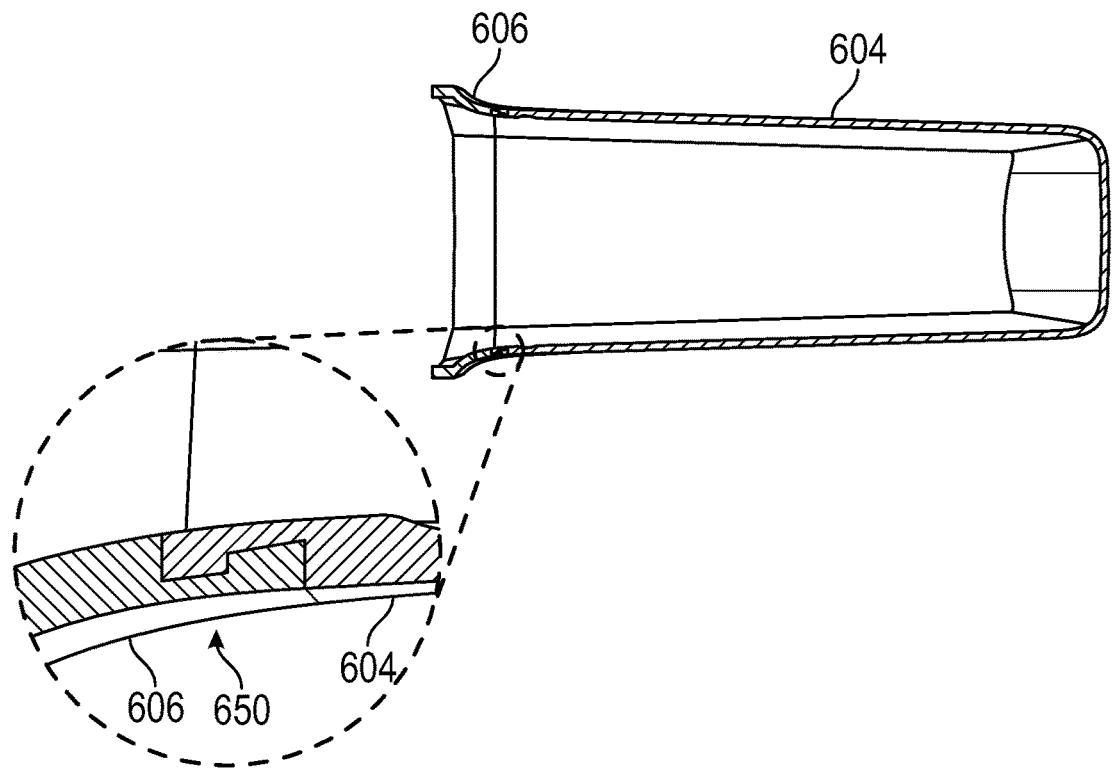

In some embodiments, the proximal and distal portions of the cover may be formed using an injection molding process. In some cases, an overmolding process is used to create a mechanical and/or chemical bond between the proximal and distal portions. FIG. 6H shows an exploded view of the cover 602, with the distal portion 604 and the proximal portion 606 separated from each other. During a molding process, the distal and proximal portions can be molded together to from a mechanical and/or chemical bond between the two. Such molding process can include injecting the first material into a mold to form the distal portion, then injecting the second material (into a different mold into or a different part of the mold) onto an edge 619 of the walls of the distal portion, thereby forming an extension of the walls of the distal portion. In some implementations, the proximal and distal portions include corresponding interlocking features 620 and 622 to strengthen the mechanical bond between the proximal and distal portions. FIGS. 6I and 6J show close-up views of the interlocking features of the proximal and distal portions. In this example, the interlocking feature of the distal portion includes a tongue and/or groove that engages with a corresponding tongue and/or groove of the proximal portion. In some cases, the interlocking feature of the distal portion is created during the first molding process using a first mold. The distal portion can then be removed from the mold or the end region of the distal portion can otherwise be exposed. Then the second material is overmolded onto the interlocking feature of the distal portion to form the corresponding interlocking feature of the proximal portion. In other cases, the proximal portion is formed first, and the distal portion is overmolded onto the proximal portion. FIG. 6K shows a section view and another close-up view (inset) of a junction region 650 between the distal portion 604 and proximal portion 606 with corresponding interlocking features molded together.

Figure 6L:
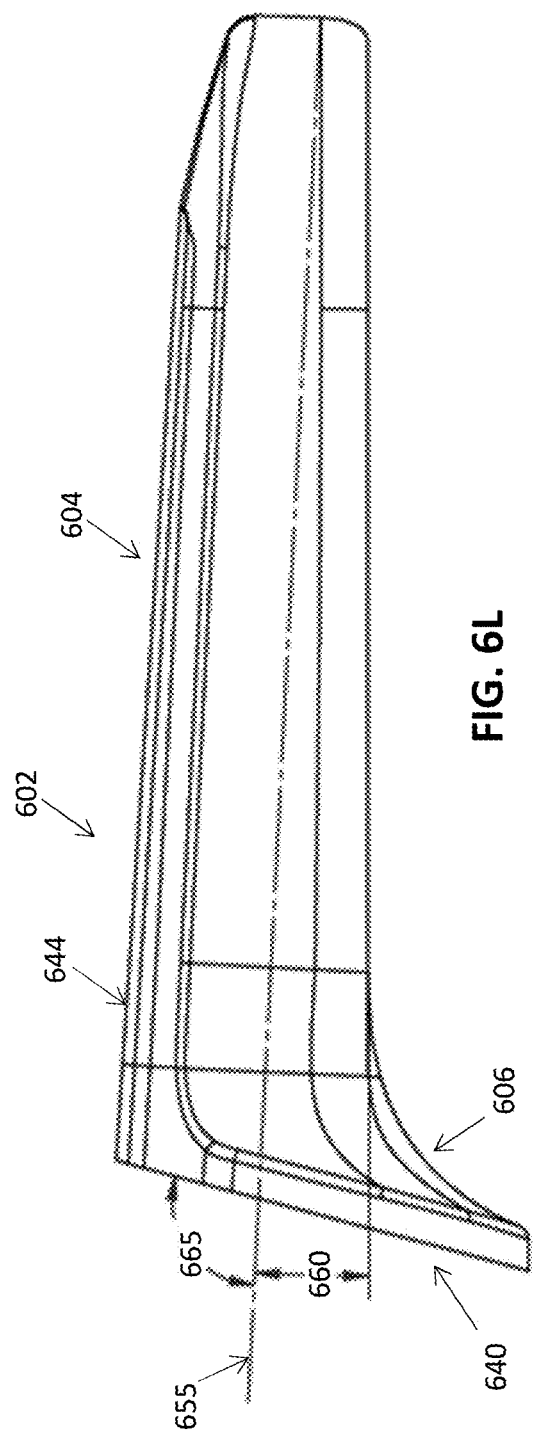

The cover may include one or more draft angles to facilitate removal of the cover from a corresponding one or more molds. FIG. 6L shows how an internal surface of one of the walls of the cover 602 can include a draft angle 660 relative to an ejection vector 655 that runs parallel to an internal surface of another wall (e.g., opposing wall) of the cover. In some embodiments, the draft angle may range from about 0.5 and 5 degrees (e.g., 0.5, 0.75, 1, 1.5, 2, 2.5, 2.75, 3, 3.5, 4, or 5 degrees). In some embodiments, instead of or in addition to the draft angle, the internal surface of the proximal portion 606 has a rough (e.g., matt) surface to facilitate removal of the cover from the mold. For example, the mold for creating the proximal portion can have a non-smooth (e.g., rough/matt) surface to form a correspondingly non-smooth surface on the proximal portion for easier removal. FIG. 6L also illustrates how the proximal end 640 of the proximal portion 606 of the cover can have a specified angle 665 relative to the ejection vector. In some embodiments, the proximal end 640 has is angled between about 95 and 120 degrees relative to the ejection vector.

Figure 7:
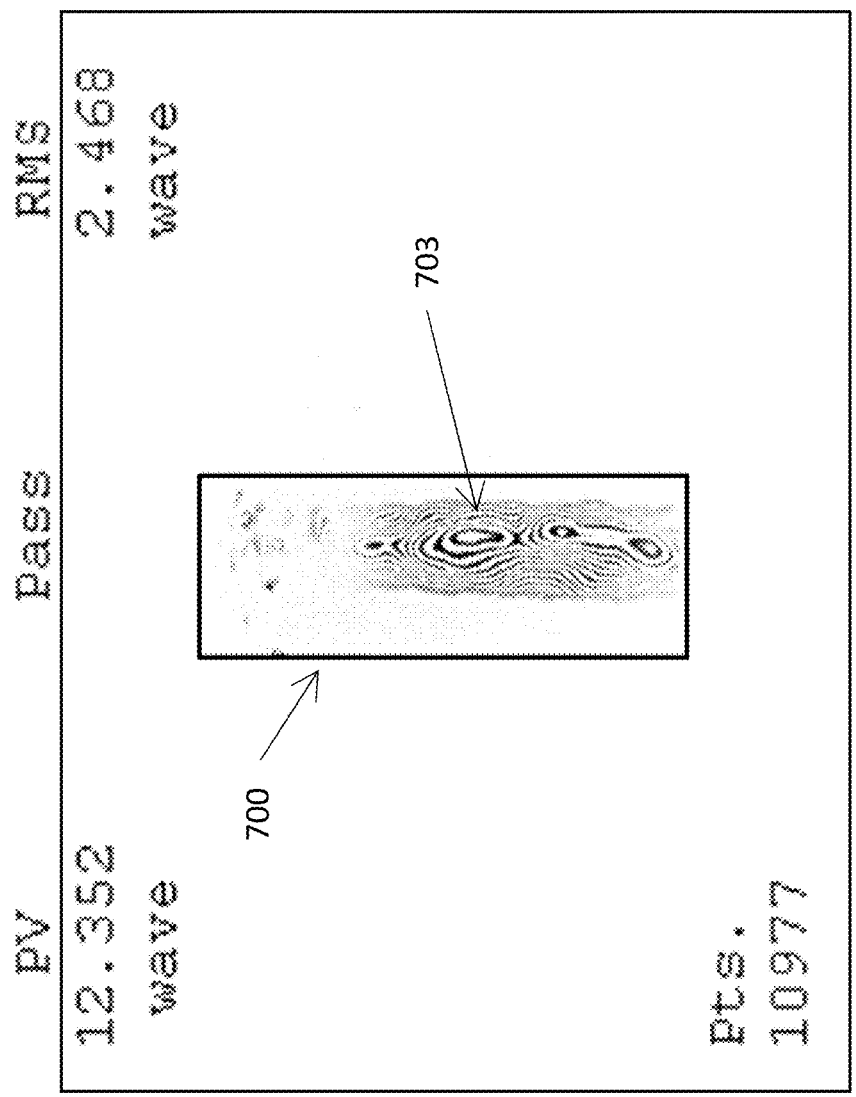
FIG. 7 illustrates an example image of a window showing non-uniformities due to an injection molding fabrication process.

In some cases, the injection molding process may affect the dimensions and/or material properties of the sleeve in a way that affects the performance of the intraoral scanner. For example, the first and/or second material may have flow characteristics when in molten form that cause the material to have distortions once hardened to solid form. Such distortions may not be significant in some applications, but may negatively affect, for example, the optical transmission properties of the window. FIG. 7 illustrates an example image of a window 700 analyzed using an optical analytical instrument. As shown, the window includes distortions 703 from an injection molding process (e.g., weave front error) indicating non-uniform material properties across the window. In this case, the window has an unacceptable amount of distortion (out of spec), and may cause an unacceptable amount of error in an intraoral scan. In a manufacturing setting, one or more of the windows (e.g., one or more per batch) can be tested for optical characteristic to identify and eliminate those that have our determined to be out of spec. Even when a window has acceptable amounts of distortion (within spec), there may be difference among different windows even using the same manufacturing process. For example, one batch of barrier devices may have windows with different optical characteristics than windows of another batch of barrier devices. In some cases, barrier devices formed using different molds may have windows with different optical characteristics. To compensate for these differences, the intraoral scanner may be calibrated based on characteristics of a particular window/barrier device, or based on characteristics of a particular batch of windows/barrier devices. Example calibration parameters can include focal length, scanning rate, scanning intensity, wavelengths, etc.

In some embodiments, the barrier devices include identifiers that may include information related to the manufacturing process. The identifiers may include information related to the optical characteristics of the windows. This information can be used to determine which barrier devices are within specification and, when within specification, what the optical characteristics. Such optical characteristics may be used to set calibration parameters or use modes of a scanner. The identifiers may be computer readable (e.g., readable by scanning). Such identifiers can include bar codes, QR codes, alphanumeric codes, logos, symbols, and/or other computer readable identifiers. In some implementations, the identifiers are readable by the intraoral scanning device itself. The identifiers may be adhered onto the barrier device (e.g., using via an adhesive sticker) and/or be imprinted on the barrier device (e.g., via a molding process). In some embodiments, the adhesive sticker is adhered onto an external surface of the widow or other external surface of the barrier device. Examples of suitable identifiers and associated methods, devices and system are described in U.S. Provisional Patent Application Nos. 62/830,336 and 62/955,662, each of which is incorporated herein by reference in its entirety. The measurement and qualification of barrier devices can be implemented in any of a number of ways during the manufacturing process. In one example, a grid target having predetermined dimensions can be added on each barrier device (e.g., as part sticker). The grid targets can be measured (e.g., using a specialized grid) and its parameters (e.g., dimensions) recorded in a database and matched to corresponding identifiers. Alternatively, each barrier device may be measured, with any deviations from nominal being recorded in a database and matched to a corresponding identifier. In some cases, barrier devices having windows that are found to be within specification can be marked with the authentication identifiers while those barrier devices having windows that are found to be out of specification will not be marked with identifiers (or marked with different identifiers), thereby preventing the out of spec barrier devices from being used with the intraoral scanner.

Figure 8A:
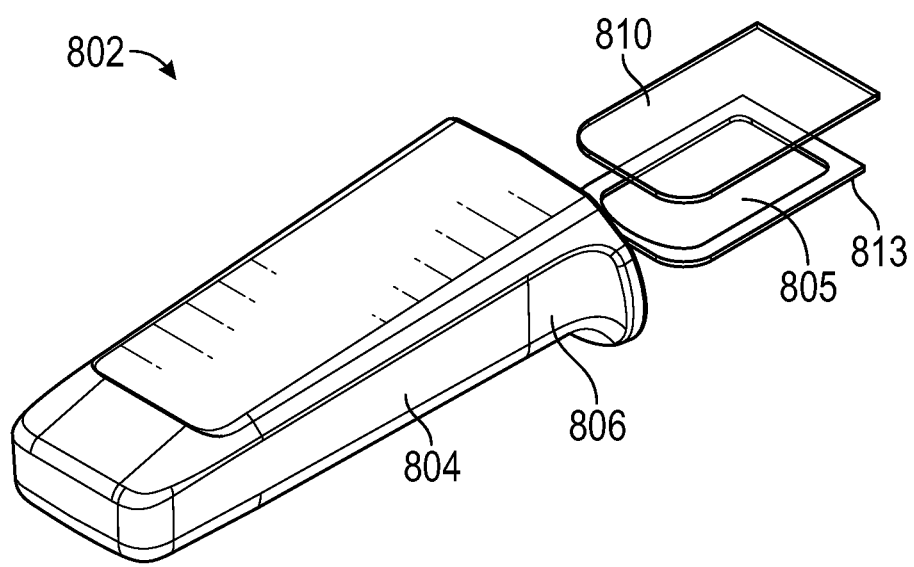
FIGS. 8A-8E illustrate a variation of the embodiment of FIGS. 6A-6I having a separately formed window.

FIGS. 8A-8E show another example barrier device that is a variation of the barrier device 600 (FIGS. 6A-6I), where the window is separately formed from the cover. FIG. 8A shows the cover 802 of the barrier device, which includes a distal portion 804, a proximal portion 806, a window 810 and a coupling member 813. The cover 802 can be coupled to a sleeve as described herein (e.g., sleeve 608). The distal and proximal portions of the cover 802 can be formed using a molding/overmolding process as described herein. The window 810 may be formed in a separate process and may be coupled to the cover via the coupling member 813. In some embodiments, the coupling member includes an adhesive, such as a pressure-sensitive adhesive, drying adhesive and/or contact adhesive. In some embodiments, the coupling member includes a spacer or backing, such as a foam spacer or backing (e.g., double-sided adhesive spacer or backing and/or may also be a gasket, welding, or liquid adhesive). The coupling member may have an opening 805 or space in accordance with an opening of the cover 802 to allow light transmission through the window. The window 810 may have optical properties as described herein. The window 810 may be made of any material sufficiently transparent for signals to pass to and/or from the intraoral scanner probe. In some embodiments, the window 810 is made of a transparent polymer material (e.g., polycarbonate and/or polymethyl methacrylate). In some cases, the window 810 is made of a different material than the distal portion 804 and/or the proximal portion 806. In some embodiments, the window 810 is made of glass and/or quartz material. In some embodiments, the window 810 has a thickness ranging from about 0.5 to about 2 mm (e.g., about 0.75 mm, about 1 mm, about 1.25 mm, about 1.5 mm, etc.). In any of the devices described herein, the window may also have AR (anti reflective) coatings or treatments implemented on one or both sides of the material. This can be done by material deposition, applying specialized optical stickers or films, and other methods).

Figure 8B:
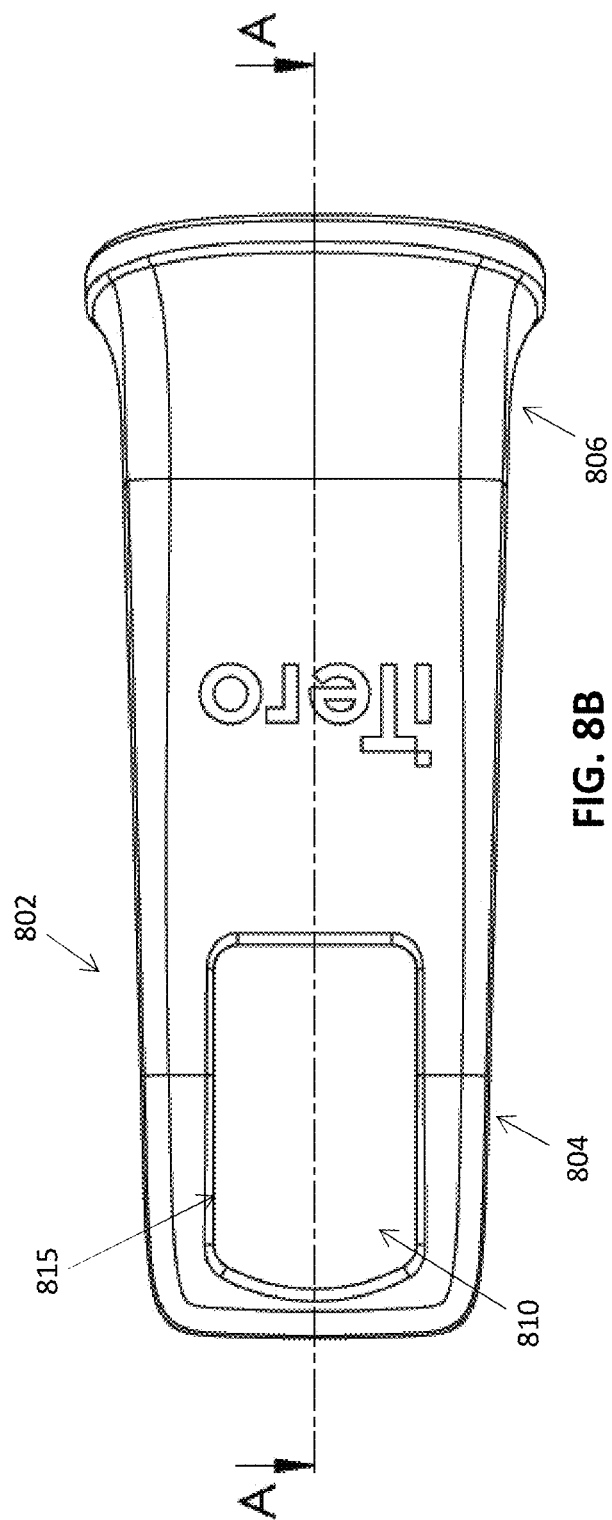
Figure 8C:
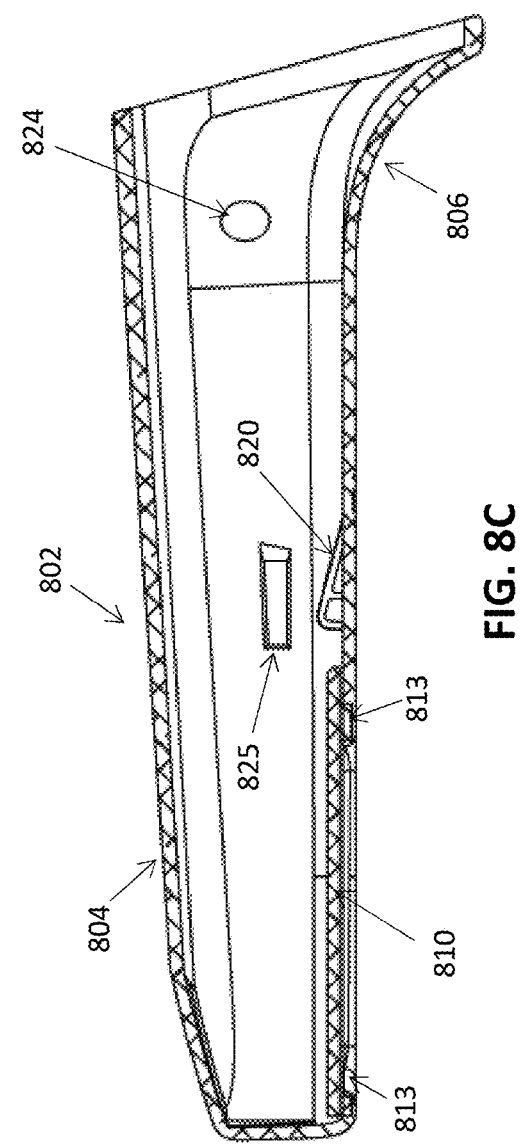
Figure 8D:
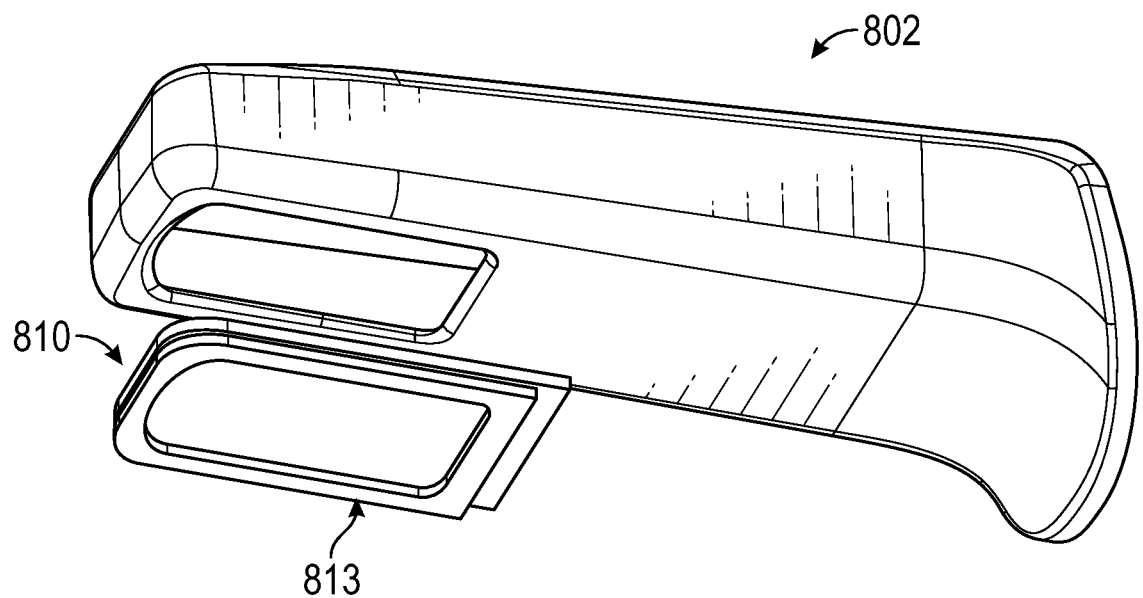
Figure 8E:
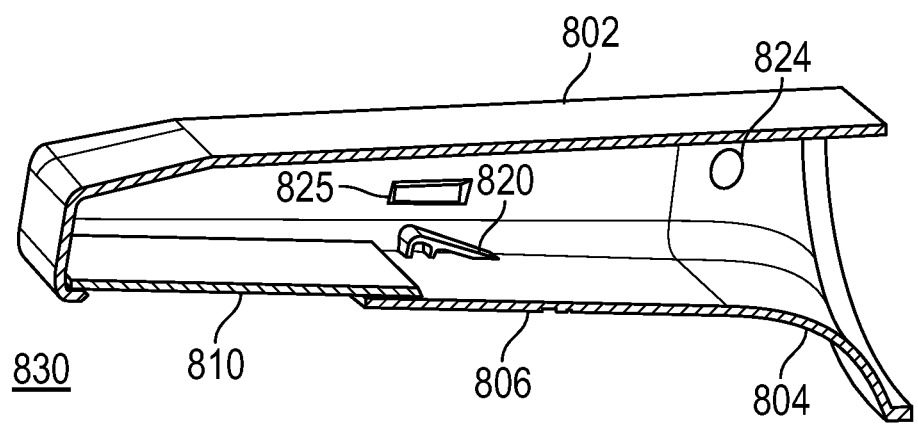

FIGS. 8B and 8C show a bottom and a side section A-A view, respectively, of the cover 802 showing the window 810 assembled therein. In this example, the window 810 can be positioned within the internal cavity of the cover and adhered onto an internal surface of the cover. The distal portion 804 can include a window opening 815 where the window is aligned and secured via the coupling member 813. The coupling member 813 can be configured to provide an adhesive barrier between the window and the cover 802. In some cases, the coupling member includes one or more sealants. In some embodiments, the cover include multiple engagement features 820, 824 and 825 configured to engage with corresponding engagement features of the scanner probe. The engagement features may include one or more protruding features (e.g., 820 and 825) and/or recessed features (e.g., 824). The engagement features may include one or more clips, hooks, clasps and/or fasteners that are configured to removably engage the barrier device to the scanner probe. FIG. 8D shows bottom perspective view of the cover 802 with the window 810 and coupling member 813 separated removed from the cover. FIG. 8E shows a section view of the cover sectioned along a plane 830.

In some embodiments, the cover 802 may include one or more draft angles (e.g., 0.5 and 5 degrees from an ejection vector) to facilitate removal of the cover from a corresponding one or more molds, such as described above referring to cover 602 (FIGS. 6A-6I). In some embodiments, instead of or in addition to the draft angle, the internal surface of the proximal portion 806 and/or distal portion 804 can have a rough (e.g., matt) surface to facilitate removal of the cover from the mold. Since the window 810 is made separately from the walls of the distal portion 804, the internal surface of the walls of the distal portion 804 may be less smooth (rougher) compared to the internal and/or external surfaces of the window 810.

Figure 9:
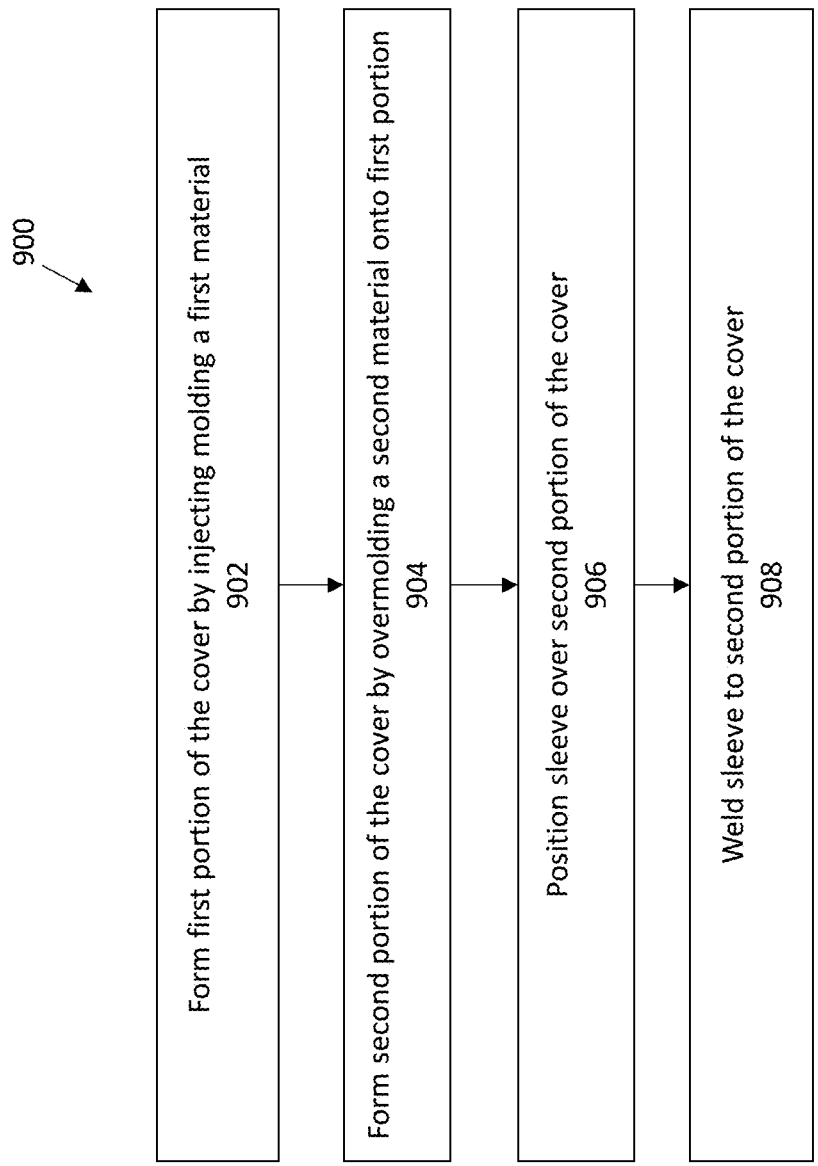
FIG. 9 is a flowchart illustrating an example process for forming a cover using an overmolding process.

FIG. 9 shows a flowchart 900 indicating a process for forming a removable barrier device for covering a probe of an intraoral scanner, according to some embodiments. Referring to 901, a first portion (e.g., distal portion) of the cover is formed by injection molding a first material. The first material may be injected into a mold having a shape in accordance to the first portion of the cover. The first portion of the cover can have an elongate shape that includes walls that define an internal cavity and a closed end to cover the distal end of the probe. In some cases, at least one of the walls of the first portion of the cover can include at least one window opening for a corresponding window. In some cases, at least one of the walls of the first portion of the cover can include at least one window formed of the first material, thereby forming a window that is integral to the at least one wall.

Referring to 904, a second portion of the cover is formed by overmolding a second material onto the first portion. The second material may be the same as the first material or different than the first material. In some implementations, the first material may be have greater optical transparency and/or rigidity than the second material. The molding process can form a seal (e.g., hermetic seal) between the first and second portions. In some cases, the first and second portions are chemically bonded to each other. In some embodiments, the second material is overmolded onto an edge of the walls of the first portion to form an extension of the walls of the first portion. In some cases, the first portion has an interlocking feature (e.g., ridge, groove, tongue, recess and/or protrusion) that the second material conforms to (e.g., while in molten form) to form a corresponding interlocking feature (e.g., ridge, groove, tongue, recess and/or protrusion) that mechanically strengthens the bond between the first and second portions. In some cases, an internal surface of one wall of the cover has a draft angle or a surface texture (roughness) to facilitate removal of the cover from the corresponding mold(s).

Referring to 906, a sleeve is positioned over the second portion of the cover. The sleeve can be a flexible polymer sheet or tube (e.g., medical grade). At 908, the sleeve is welded to the second portion of the sleeve, e.g., by heating the sleeve and/or the second portion of the cover. The welding process can form a seal (e.g., hermetic seal) between the sleeve and the second portion. After the barrier device is formed, one or more testing procedures can be implemented to test the efficacy of the barrier device, as described herein, for acting as a biological barrier.

Antireflective Materials

Any of the apparatuses described herein may include one or more antireflective materials, and in particular an antireflective material that is appropriate for the near-IR range of frequencies of light. For example, any of these apparatuses may be include an antireflective material on the window of the removable barrier devices. The antireflective material may be formed of a nanostructured material (e.g., "moth eye" material). This material may be applied as a laminated layer that is applied to the device (e.g., to the window). The material may be a hydrophobic material that is applied to the sleeve/removable protective cover of the device or, in particular, to the removable window a barrier that is applied over the intraoral scanner.

Reflections, such as specular reflections, are particularly problematic in intraoral scanners that have a high level of back reflections off of the window to the camera within the intraoral scanner, e.g., when the window for the intraoral scanner is located close to the focal point of the sensor (e.g., within a few cm), and/or where internal polarizers may not be used, e.g., because the polarization depth is insufficient.

Thus, described herein are methods and apparatuses (e.g., devices) in which an anti-reflective layer is included (e.g., on the intraoral scanner window and/or the window of the removable barrier for the intraoral scanner). An antireflective layer may be a structure, e.g., coating, film or lamination, that is applied to the window of the intraoral scanner window and/or the window of the removable barrier. In some variations the anti-reflective structure is a nanostructure that is configured as an anti-reflective material configured to reduce or eliminate reflections, in particular reflections in the near-IR range of light. The anti-reflective material may be a nanostructure arrays (NSAs); these materials may include silicon and non-silicon materials (e.g., nanoporous $SiO_2$) and may have a structure that is configured to operate as an anti-reflective material in the nanostructured range.

The anti-reflective structure may be a hydrophobic structure forming a nanostructured film that reduces or eliminates reflections. A typical "moth eye" anti-reflective structure may have a hexagonal pattern of nanoscale bumps that are smaller than the wavelength of the light applied (e.g., in this case, near-IR light). In some examples, anti-reflective structures that may be used include stickers of material that may be laminated to a window to prevent or reduce reflection.

An intraoral 3D scanners may include a window with an anti-reflective coating by layer deposition in vacuum chamber. In particular, described herein are removable protective covers/sleeves for intraoral scanners having a window with a hydrophobic (moth eye) anti-reflective structure. These apparatuses (e.g., devices) and methods, e.g., methods of implementing the antireflective structures as described herein may include direct lamination of a material (e.g., as a "sticker") on a molded sleeve/removable barrier for the intraoral scanner. The anti-reflective material ("sticker") may be laminated on a glass/polymer window, e.g., by applying the sticker that has the nanoscale structure forming the moth-eye antireflective coating already formed, and the window assembly including the laminated antireflective sticker may be combined with the body of the sleeve/protective cover, as described above. In general, the moth eye structure may be added to the window as part of an injection molding process of the window or of the whole sleeve/protective cover.

In general, the nanostructured (e.g., "moth eye") antireflective structures described herein may be formed and applied to the window as a sticker or lamination; alternatively or additionally, these nanostructured antireflective surfaces may be formed as a coating or layer directly on the window (e.g., without using a "sticker" configuration, which may include an additional adhesive material). In some variations the antireflective structures described herein may be formed directly on the window.

The anti-reflective laminated "stickers" described herein may be particularly advantageous. For example, these structures may be formed at relatively low cost (e.g., as compared to class anti-reflective coatings), and can be added to glass or polymeric windows for removable protective covers/sleeves for intraoral scanners. These structures may achieve similar anti-reflective performances on glass or polymer windows. The laminated (e.g., sticker) configuration described herein may allow the antireflective material to be fabricated separately from the window, which may allow the formation of even complex antireflective designs (e.g., nanostructures) that may include multiple layers deposed on a substrate, even where multiple layers requires higher temperatures for formation. By fabricating the anti-reflective sticker with an antireflective coating separately from the window, this may avoid damaging the window, and in particular, may avoid heat damage to polymeric windows. In general, these methods and device may have very high performance antireflective coatings.

The anti-reflective materials described herein may have a very high antireflection performances of over wide spectral range and wide angle of incidence range, particularly as compared to other antireflective coating methods such as layer deposition.

The anti-reflective material may be on the outside of the window (e.g., facing the patient. In some variations, the antireflective material may be on the inside of the window (e.g., facing the intraoral scanner; in some variations an anti-reflective material may be on both the inside and outside of the window. It may be particularly advantageous to include the antireflective (e.g., "moth eye") material on the outside of the window, as it may be also be hydrophobic, and may help keep saliva from spreading on the window.

Figure 10A:
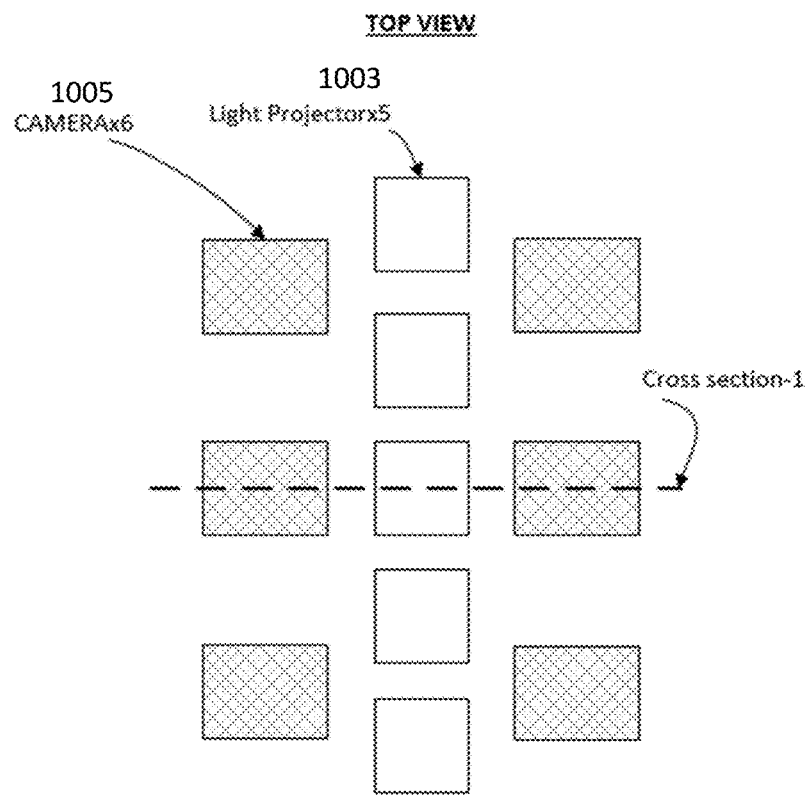
FIG. 10A schematically illustrates one example of an intraoral scanner.
Figure 10B:
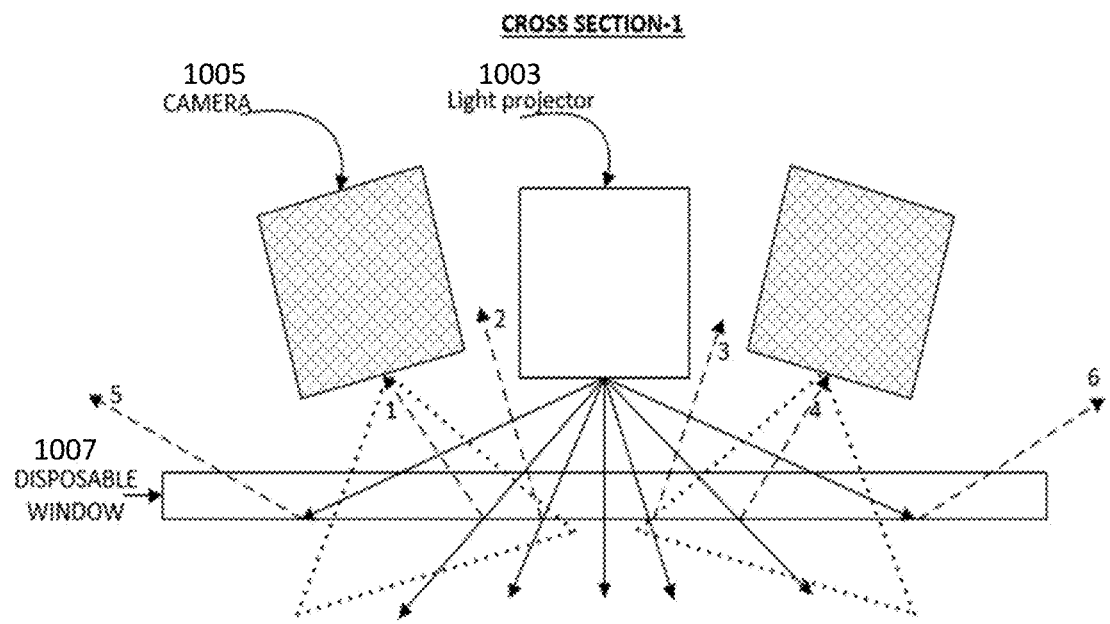
FIG. 10B is a section through the intraoral scanner of FIG. 10A, showing internal reflection of a window.

FIG. 10A illustrates one example of a schematic of an example of an intraoral scanner as described herein. In this example, the intraoral scanner consists of 5 light projectors 1003 and 6 cameras 1005 disposed as illustrated. FIG. 10B shows the cross-section through the intraoral scanner shown by the dashed line in FIG. 10A. In FIG. 10B, the two cameras 1005 are arranged at an angle to the light projector 1003 and directed out through the window 1007. The arrangement of the cameras 1005, projector 1003, and disposable window 1007 (which may be on the sleeve/removable barrier for the intraoral scanner) may cause some of the rays generated by the light projectors to be reflected by the window 1007 and reach the entrance pupil of the cameras 1005. In FIG. 10B, the dashed arrows 1, 4 reach the camera entrance pupils and then the camera sensor surfaces (although other internally reflected light 5, 2, 3, 6 is not passed on to the cameras). The internally reflected signals reaching the camera sensor is the internal reflections, and may significantly decrease the signal to noise (SNR) of the system; the internal reflection may blind the image in the location of the reflection, limiting or preventing collection of data in this location.

Figure 10C:
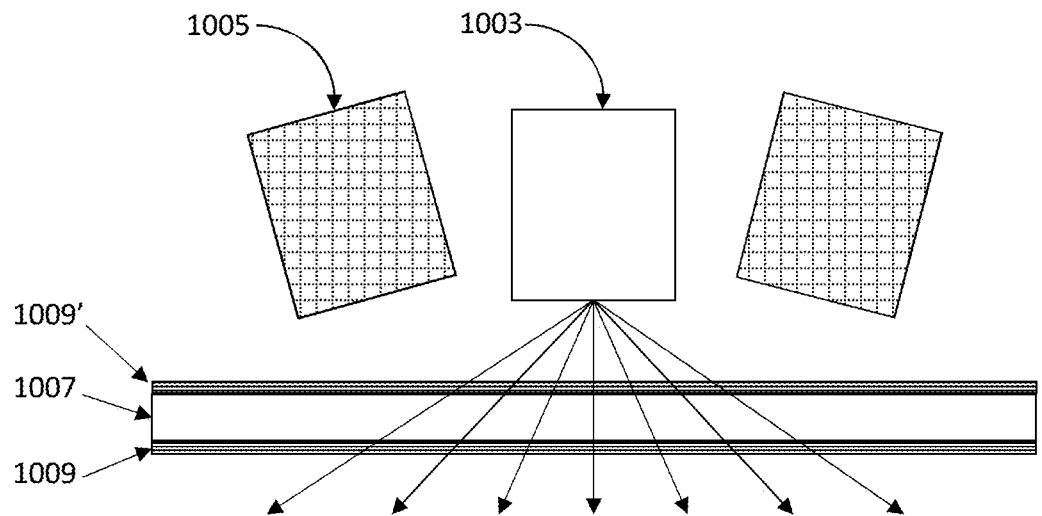
FIG. 10C is a section through the intraoral scanner of FIG. 10A, in which the window includes an anti-reflective material to prevent or reduce internal reflection.

The antireflective material (antireflective structure) 1009, 1009' described herein may be applied on the window 1007 and may reduce/remove the internal reflection. The antireflective material may include a nanostructure (forming the moth eye structure) that is oriented to prevent internal reflection from within the window, while permitting light returning from the teeth. In some variations, as mentioned above, both sides of the window may include the antireflective material, as shown in FIG. 10C.

Figure 11:
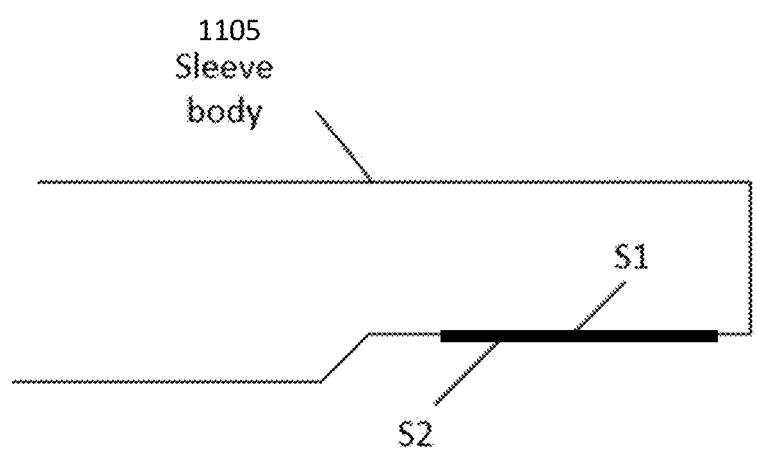
FIG. 11 is a schematic of a sleeve including a window on which anti-reflective material has been included on both the inner surface (S1) and outer surface (S2) of the window.

In some variations the device may include a window (e.g., on the sleeve/removable barrier for the intraoral scanner) onto which the antireflective material (e.g., a moth eye nanostructured material) is attached. The nanostructured antireflective material (which may be configured to pass both visible light and/or near infrared light) may be laminated on the window. For example, the moth eye (nanostructured antireflective material) may be configured as a sticker; the sticker may be laminated to a molded sleeve 1105 in both internal (S1) and external (S2) surfaces, as shown in FIG. 11. A sticker including the nanostructured surface forming the antireflective (moth eye) material may therefore be attached to both the internal and external surfaces during manufacturing. The window may then be assembled to the sleeve//removable barrier for the intraoral scanner, as described herein.

Alternatively, in some variations, the method of forming the window of the sleeve may include forming the nanostructured antireflective material on the optical window. For example, in some variations the window may be formed by an injection molding process in which the mold for injection molding of the window includes the nanostructure (e.g., a pattern of hexagonal nanoscale projections). For example, the moth eye antireflective nanostructure may be implemented during the injection molding process of the sleeve optical window, and the window may then be assembled to sleeve body. In some variations the moth eye antireflective nanostructure may be implemented during the injection molding process of the whole sleeve body.

In addition to the intraoral scanners described herein, these methods and materials (e.g., stickers of nanostructured antireflective materials) may be used as part of any optical system having a similar geometrical arrangement as described herein.

The nanostrcuture may be, e.g., a pattern of hexagonal and/or hexagonally arranged projections having a height of between 100 nm and 900 nm (e.g., between 200 nm and 800 nm, between 250 nm and 700 nm), a pitch of between about 20 nm and 1000 nm (e.g., between 30 nm and 900 nm, etc.) and a gap of between about 100 nm and 600 nm (e.g., between about 200 nm and 500 nm, etc.). In some variations multiple layers of the nanoscale pattern (of projections) may be placed atop each other (e.g., 2 layers, 3 layers, etc.); each layer may be different in material (e.g., $SiO_2$, $Al_2O_3$, $MgF_2$, $TiO_2$, InSb, ZnO, $ZrO_2$, HgCdTe, Ge, etc.). The nanostructures may be formed one a substrate comprising the same or a different material (e.g., Si, etc.).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A removable barrier device for covering a handheld intraoral scanner, the removable barrier device comprising:
a cover adapted to fit over a probe of the scanner, the cover including:
a distal portion having walls defining an internal cavity for accommodating a distal end of the probe and formed of a first material, wherein at least one of the walls includes at least one window for allowing transmission of an optical signal between the probe and an external environment; and
a proximal portion coupled to the distal portion; and
a flexible sleeve adapted to cover a handle of the scanner, the flexible sleeve coupled to the proximal portion of the cover at an interface region configured to prevent fluid from passing through the barrier device between the cover and the sleeve.

2. The device of claim 1, wherein the proximal portion is molded to the distal portion.

3. The device of claim 1, wherein the proximal portion is formed of a second material different than the first material.

4. The device of claim 1, wherein the flexible sleeve is welded to the proximal portion of the cover at the interface region.

5. The device of claim 1, wherein the flexible sleeve is more flexible than the proximal portion of the cover.

6. The device of claim 1, wherein the flexible sleeve is more flexible than the distal portion of the cover.

7. The device of claim 1, wherein the first material comprises a polycarbonate or a polymethyl methacrylate material.

8. The device of claim 3, wherein the second material comprises a thermoplastic elastomer material.

9. The device of claim 3, wherein the first material is more rigid than the second material at room temperature.

10. The device of claim 1, wherein the walls of the distal portion have an inner surface including one or more engagement features configured to engage with corresponding engagement features of the probe.

11. The device of claim 1, wherein an internal surface of one of the walls includes a draft angle ranging from 0.5 and 5 degrees with respect to an ejection vector that runs parallel to an internal surface of another wall of the cover.

12. The device of claim 1, wherein the at least one window has a thickness ranging from 0.5 mm and 3 mm.

13. The device of claim 1, wherein the at least one window has a refractive index of ranging from 1.4 and 1.8.

14. The device of claim 1, wherein the device includes an identifier associated with an optical property of the at least one window.

15. The device of claim 1, wherein the at least one window is made of the first material and is integrally formed with at least one of the walls of the distal portion.

16. A method of forming a removable barrier device for covering a handheld intraoral scanner, the method comprising:
    forming a cover adapted to fit over a probe of the scanner by:
        forming a distal portion of the cover by injecting molding a first material, wherein the distal portion includes walls that define an internal cavity, one of the walls including at least one window opening or at least one window formed of the first material;
        forming a proximal portion of the cover by coupling a second material to the first material such that the second material is bonded to the first material, wherein the second material is the same as or is different from the first material, further wherein the proximal portion is bonded to an edge of the walls of the distal portion to form an extension of the walls of the distal portion; and
    bonding a flexible sleeve to the proximal portion of the cover such that an interface region between the flexible sleeve and the proximal portion of the cover is resistant to fluid from passing therethrough, wherein the sleeve is adapted to cover a handle of the scanner and is more flexible than the distal portion of the cover.

17. The method of claim 16, wherein forming the proximal portion comprises overmolding the second material on an interlocking feature along the edge of the distal portion to form a corresponding interlocking features in the proximal portion.

18. The method of claim 16, wherein bonding the flexible sleeve to the proximal portion of the cover includes heating one or both of the flexible sleeve and the proximal portion to weld the flexible sleeve to the proximal portion.

19. The method of claim 16, wherein forming the cover includes forming one or more engagement features on in inner surface of one or both of the distal and proximal portions of the cover, the one or more engagement features configured to engage with corresponding engagement features of the probe.

20. The method of claim 16, wherein forming the cover includes forming an internal surface of one wall of the cover with a draft angle ranging from 0.5 and 5 degrees with respect to an ejection vector that runs parallel to an internal surface of another wall of the cover.

21. The method of claim 16, wherein forming the cover includes forming an internal surface of at least one wall of the cover with a surface roughness greater than an internal surface of the at least one window of the barrier device.

22. The method of claim 21, further comprising coupling the at least one window to the internal surface of the one wall of the cover.

23. The method of claim 16, further comprising testing the barrier device by filling an inside of the barrier device with water, waiting a predetermined time, and inspecting outside surfaces of the barrier device for evidence of water leakage.

* * * * *